(12) United States Patent
Sina et al.

(10) Patent No.: US 9,820,889 B2
(45) Date of Patent: Nov. 21, 2017

(54) METHOD OF MANUFACTURING AN ABSORBENT ARTICLE HAVING FULLY ENCIRCLING BODYSIDE AND GARMENT-SIDE WAISTBAND

(71) Applicant: Kimberly-Clark Worldwide, Inc., Neenah, WI (US)

(72) Inventors: Joseph J. Sina, Appleton, WI (US); Kathleen Irene Bennett, Neenah, WI (US); Marcille Faye Ruman, Oshkosh, WI (US); Thomas Harold Roessler, Menasha, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 918 days.

(21) Appl. No.: 14/068,918

(22) Filed: Oct. 31, 2013

(65) Prior Publication Data
US 2015/0119219 A1   Apr. 30, 2015

(51) Int. Cl.
*B31F 7/00*   (2006.01)
*A61F 13/15*   (2006.01)

(52) U.S. Cl.
CPC .. *A61F 13/15723* (2013.01); *A61F 13/15699* (2013.01)

(58) Field of Classification Search
CPC ............ A61F 13/4902; A61F 13/49009; A61F 13/49011

(Continued)

(56) References Cited

U.S. PATENT DOCUMENTS 1,397,579 A   11/1921   Guinzburg
4,100,324 A   7/1978   Anderson et al.
(Continued)

FOREIGN PATENT DOCUMENTS

EP   0459178   12/1991
EP   0217032   2/1992
(Continued)

OTHER PUBLICATIONS

Notification of Transmittal of the International Search Report and the Written Opinion of the International Searching Authority for International Application No. PCT/IB2014/065277, dated Feb. 26, 2015; 14 pages.
(Continued)

*Primary Examiner* — Robert Long
*Assistant Examiner* — Eyamindae Jallow
(74) *Attorney, Agent, or Firm* — Armstrong Teasdale LLP

(57) ABSTRACT

A method for manufacturing absorbent articles comprises delivering a continuous web assembly including a backsheet material, a liquid permeable bodyside liner material, and an absorbent structure interposed between the backsheet material and the bodyside liner material, the web assembly having a body-facing side and a garment-facing side; attaching a discrete segment of first waist elastic material to the body-facing side of the web assembly; attaching a discrete segment of second waist elastic material to the garment-facing side of the web assembly such that the web assembly is interposed between the discrete segments of first and second waist elastic materials; and cutting the web assembly to form a plurality of absorbent articles.

24 Claims, 17 Drawing Sheets

(58) Field of Classification Search
USPC ....... 493/343, 344, 346, 347, 374, 378, 379, 493/381, 394, 405

See application file for complete search history.

(56) References Cited

U.S. PATENT DOCUMENTS

| | | | |
|---|---|---|---|
| 4,205,679 A | 6/1980 | Repke et al. | |
| 4,573,986 A | 3/1986 | Minetola et al. | |
| 4,597,760 A | 7/1986 | Buell | |
| 4,610,681 A | 9/1986 | Strohbeen et al. | |
| 4,663,220 A | 5/1987 | Wisneski et al. | |
| 4,699,621 A | 10/1987 | Stevens et al. | |
| 4,701,172 A | 10/1987 | Stevens | |
| 4,747,846 A | 5/1988 | Boland et al. | |
| 4,846,825 A | 7/1989 | Enloe et al. | |
| 4,940,464 A | 7/1990 | Van Gompel et al. | |
| 5,000,806 A * | 3/1991 | Merkatoris | A61F 13/15601 156/161 |
| 5,046,272 A | 9/1991 | Vogt et al. | |
| 5,064,421 A | 11/1991 | Tracy | |
| 5,104,116 A | 4/1992 | Pohjola | |
| 5,224,405 A | 7/1993 | Pohjola | |
| 5,226,992 A | 7/1993 | Morman | |
| 5,236,430 A | 8/1993 | Bridges | |
| 5,284,703 A | 2/1994 | Everhart et al. | |
| 5,350,624 A | 9/1994 | Georger et al. | |
| 5,385,775 A | 1/1995 | Wright | |
| 5,476,458 A | 12/1995 | Glaug et al. | |
| 5,482,765 A | 1/1996 | Bradley et al. | |
| 5,486,166 A | 1/1996 | Bishop et al. | |
| 5,490,846 A | 2/1996 | Ellis et al. | |
| 5,492,751 A | 2/1996 | Butt, Sr. et al. | |
| 5,496,429 A | 3/1996 | Hasse et al. | |
| 5,500,063 A * | 3/1996 | Jessup | A61F 13/15601 156/160 |
| 5,593,401 A | 1/1997 | Sosalla et al. | |
| 5,601,544 A | 2/1997 | Glaug et al. | |
| 5,607,416 A | 3/1997 | Yamamoto et al. | |
| 5,624,420 A | 4/1997 | Bridges et al. | |
| 5,624,424 A | 4/1997 | Sausaka et al. | |
| 5,662,638 A | 9/1997 | Johnson et al. | |
| 5,706,524 A | 1/1998 | Herrin et al. | |
| 5,714,156 A | 2/1998 | Schmidt et al. | |
| 5,766,389 A | 6/1998 | Brandon et al. | |
| 5,772,825 A | 6/1998 | Schmitz | |
| 5,779,831 A | 7/1998 | Schmitz | |
| 5,820,973 A | 10/1998 | Dodge, II et al. | |
| 5,870,778 A | 2/1999 | Tharpe et al. | |
| 5,885,266 A | 3/1999 | Chihani et al. | |
| 6,057,024 A | 5/2000 | Mleziva et al. | |
| 6,113,717 A | 9/2000 | Vogt et al. | |
| 6,369,291 B1 | 4/2002 | Uchimoto et al. | |
| 6,380,292 B1 | 4/2002 | Gibes et al. | |
| 6,383,170 B1 | 5/2002 | Mishima et al. | |
| 6,394,991 B1 | 5/2002 | Takei et al. | |
| 6,508,797 B1 | 1/2003 | Pozniak et al. | |
| 6,552,245 B1 | 4/2003 | Roessler | |
| 6,562,017 B1 | 5/2003 | Nakaoka et al. | |
| 6,576,809 B2 | 6/2003 | Inoue et al. | |
| 6,585,840 B2 | 7/2003 | Rabe et al. | |
| 6,605,071 B1 | 8/2003 | Gray et al. | |
| 6,605,173 B2 | 8/2003 | Glaug et al. | |
| 6,645,190 B1 | 11/2003 | Olson et al. | |
| 6,753,455 B2 | 6/2004 | Chmielewski | |
| 6,822,136 B1 | 11/2004 | Niemeyer et al. | |
| 6,899,780 B2 | 5/2005 | Rajala et al. | |
| 6,916,750 B2 | 7/2005 | Thomas et al. | |
| 6,939,335 B2 | 9/2005 | Franke et al. | |
| 6,962,578 B1 | 11/2005 | Lavon et al. | |
| 6,969,378 B1 | 11/2005 | Vukos et al. | |
| 6,969,441 B2 | 11/2005 | Welch et al. | |
| 7,014,632 B2 | 3/2006 | Takino et al. | |
| 7,047,572 B2 | 5/2006 | Hopkins | |
| 7,227,051 B2 | 6/2007 | Mitsui et al. | |
| 7,264,686 B2 | 9/2007 | Thorson et al. | |
| 7,666,175 B2 | 2/2010 | Trennepohl | |
| 7,727,217 B2 | 6/2010 | Hancock-Cooke | |
| 7,777,094 B2 | 8/2010 | Mori et al. | |
| 7,794,441 B2 | 9/2010 | Ashton et al. | |
| 7,803,244 B2 | 9/2010 | Siqueira et al. | |
| 7,854,022 B2 | 12/2010 | Warren et al. | |
| 7,901,390 B1 | 3/2011 | Ashton et al. | |
| 8,109,916 B2 | 2/2012 | Wennerback | |
| 8,168,028 B2 | 5/2012 | Schneider et al. | |
| 8,212,102 B2 | 7/2012 | Kumasaka | |
| 8,282,616 B2 | 10/2012 | Lehto et al. | |
| 8,361,913 B2 | 1/2013 | Siqueira | |
| 8,506,544 B2 * | 8/2013 | Ashton | A61F 13/49015 604/385.24 |
| 9,265,669 B2 * | 2/2016 | Bennett | A61F 13/49011 |
| 9,320,655 B2 * | 4/2016 | Schoultz | A61F 13/15747 |
| 2002/0092604 A1 | 7/2002 | McCabe et al. | |
| 2003/0000620 A1 | 1/2003 | Herrin et al. | |
| 2004/0064125 A1 | 4/2004 | Justmann et al. | |
| 2004/0102757 A1 | 5/2004 | Olson | |
| 2005/0010188 A1 | 1/2005 | Glaug et al. | |
| 2006/0149208 A1 | 7/2006 | Carr | |
| 2006/0247591 A1 | 11/2006 | Hughes et al. | |
| 2007/0073262 A1 | 3/2007 | Babusik et al. | |
| 2007/0173782 A1 | 7/2007 | LaVon et al. | |
| 2007/0208318 A1 | 9/2007 | Loritz et al. | |
| 2008/0132863 A1 | 6/2008 | Waksmundzki et al. | |
| 2008/0134487 A1 | 6/2008 | Harlono | |
| 2008/0287897 A1 | 11/2008 | Guzman Reyes et al. | |
| 2009/0157034 A1 | 6/2009 | Mattingly et al. | |
| 2010/0049155 A1 | 2/2010 | Soderbergh et al. | |
| 2010/0063468 A1 | 3/2010 | Lehto et al. | |
| 2010/0076390 A1 | 3/2010 | Norrby et al. | |
| 2011/0092941 A1 | 4/2011 | Ruman et al. | |
| 2011/0125122 A1 | 5/2011 | Thorson et al. | |
| 2012/0061016 A1 | 3/2012 | Lavon et al. | |
| 2012/0241078 A1 * | 9/2012 | Schlinz | A61F 13/15601 156/73.1 |
| 2012/0316523 A1 | 12/2012 | Hippe et al. | |
| 2013/0304013 A1 | 11/2013 | Goerg-Wood et al. | |
| 2013/0338623 A1 | 12/2013 | Kinoshita et al. | |

FOREIGN PATENT DOCUMENTS

| | | |
|---|---|---|
| EP | 0638304 | 3/1999 |
| EP | 0941727 | 9/1999 |
| EP | 0955976 | 3/2002 |
| EP | 2022453 | 2/2009 |
| GB | 2250921 | 6/1992 |
| JP | 2007195792 | 8/2007 |
| WO | 0037009 | 6/2000 |
| WO | 0187211 A1 | 11/2001 |
| WO | 0188245 | 11/2001 |
| WO | 2012134444 A1 | 10/2012 |

OTHER PUBLICATIONS

Extended European Search Report for Application No. 14859257.9, Apr. 19, 2017, 8 pages.

* cited by examiner

METHOD OF MANUFACTURING AN ABSORBENT ARTICLE HAVING FULLY ENCIRCLING BODYSIDE AND GARMENT-SIDE WAISTBAND

FIELD

The present invention relates generally to a method of manufacturing absorbent articles, and more particularly to a method of manufacturing absorbent articles having bodyside and garment-side waistbands configured to fully encircle a waist of a wearer.

BACKGROUND

Exemplary absorbent articles include training pants, diapers, incontinence products, disposable underwear, medical garments, absorbent swim wear, and the like. Training pants (albeit, not exclusively) are disposable absorbent articles configured for use in the toilet training process. Toilet training is a process that includes many training techniques and aids that can be used by parents or other caregivers. One aspect of the total toilet training process is changing from the use of diapers to the use of training pants to help the child understand that he or she should now use the toilet.

Many caregivers underestimate the difficulty of teaching the toilet training process to young children. If a child does not respond to an initial toilet training instruction or introduction, the caregiver can be at a loss for finding techniques, methods, or teaching tools to encourage the child to master the art of toilet training. Thus, while various teaching tools such as books, videotapes, charts with stickers, personalized toilets, and interactive toilet training kits are available, there remains a need for improved motivational mechanisms to facilitate the toilet training process.

One motivational mechanism is the use of training pants having an improved aesthetic appearance. Specifically, a child is encouraged to wear a garment that resembles underwear worn by older children. Thus, there is an ongoing need to increase the appeal of the toilet training process to children, and to improve the aesthetic appearance of training pant. However, it is important that any modifications to the training pants to meet these needs do not compromise the use of the articles or any functional features of the articles (e.g., wetness indicators, absorbency, leakage protection, etc.).

Current training pants typically include an outer cover, a bodyside liner, and an absorbent structure disposed between the outer cover and the topsheet. Some known training pants include outwardly extending front and back side portions that can be joined together, either permanently or refastenably, in respective pairs to form sides of the pant. An elastic waistband material is often bonded between the outer cover and the bodyside liner, or to the body-facing side of the bodyside liner, adjacent one or both of the longitudinal ends of the training pant to define a gathered waistband. The elastic waistband material is often not readily visible to either the caregiver or the wearer. Further, the elastic waistband material is typically positioned only within a central portion of the training pant. The side portions of the training pant (i.e., the front and back side portions) are often free from the waistband material. That is, the waistband material is not typically located on the side portions of the training pant.

Thus, the waistband material of conventional training pants is typically discontinuous, extends around only a portion of a wearer's waist during use, and is not readily visible from either the garment-facing side or the body-facing side of the training pant. Moreover, the gathers formed by the waistband, which are often only in a central portion of the training pant, are absent from the side portions. As a result, current training pants have a waistband that is significantly and obviously different from typical underwear, which typically have a fully encircling waistband visible from the body-facing side and the garment-facing side. In addition, the discontinuous waistband of typical training pants detracts from their aesthetic appearance.

Accordingly, there is a need for a training pant having fully encircling bodyside and garment-side waistbands and a manufacturing method that enables a waistband to be placed on the bodyside and garment-side of a training pant to form a fully encircling waistband.

SUMMARY

In one aspect, a method for manufacturing absorbent articles is described. The method comprises delivering a continuous web assembly including a backsheet material, a liquid permeable bodyside liner material, and an absorbent structure interposed between the backsheet material and the bodyside liner material, the web assembly having a body-facing side and a garment-facing side; attaching a discrete segment of first waist elastic material to the body-facing side of the web assembly; attaching a discrete segment of second waist elastic material to the garment-facing side of the web assembly such that the web assembly is interposed between the discrete segments of first and second waist elastic materials; and cutting the web assembly to form a plurality of absorbent articles.

In another aspect, a method for manufacturing absorbent articles is described. The method comprises providing an absorbent assembly including a liquid permeable bodyside liner, and an absorbent structure underlying the bodyside liner material; delivering a continuous web of chassis material having a body-facing side and a garment-facing side; attaching the absorbent assembly to the web of chassis material to form a continuous web assembly; attaching a discrete segment of first waist elastic material to at least one of the body-facing side of the chassis material and the absorbent assembly; attaching a discrete segment of second waist elastic material to the garment-facing side of the chassis such that the chassis is interposed between the discrete segments of first and second waist elastic materials; and cutting the web assembly to form a plurality of absorbent articles.

In yet another aspect, a method for manufacturing absorbent articles is described. The method comprises delivering a continuous web of liquid impermeable backsheet material in a machine direction; delivering a continuous web of liquid permeable bodyside liner material in the machine direction; providing a plurality of absorbent structures; attaching the web of backsheet material to the web of bodyside liner material such that the absorbent structures are interposed between the web of backsheet material and the web of bodyside liner material; delivering a continuous web of first waist elastic material in the cross-machine direction; cutting the web of first waist elastic material to form a plurality of discrete first waist elastic members; attaching the first waist elastic members to the web of bodyside liner material in the cross-machine direction; delivering a continuous web of second waist elastic material in the cross-machine direction; cutting the web of second waist elastic material to form a plurality of discrete second waist elastic members; and attaching the second waist elastic members to the web of backsheet material in the cross-machine direction such that the webs of backsheet material and bodyside liner material are interposed between one of the first waist elastic members and a respective one of the second waist elastic members.

Other features of the invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
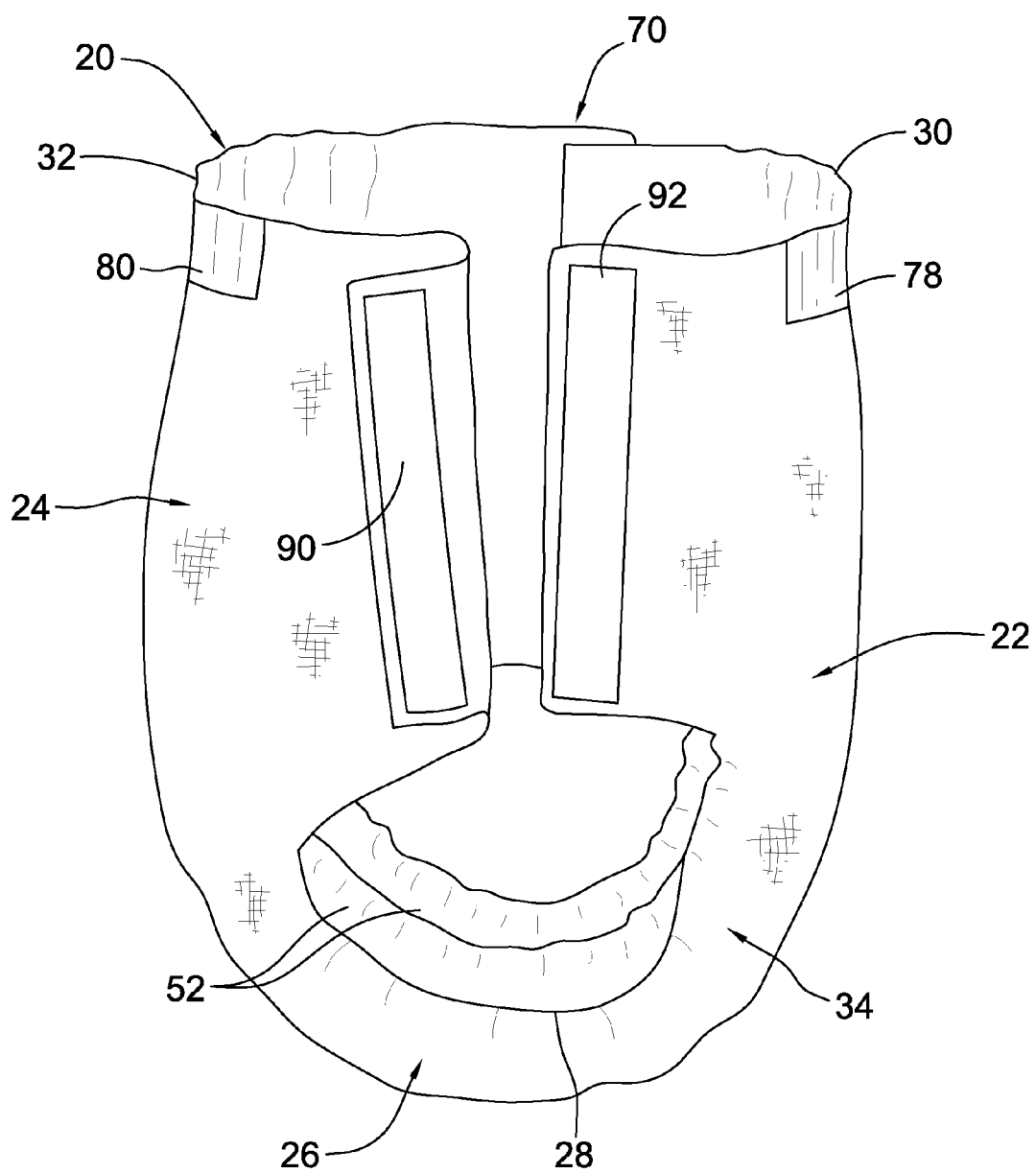
FIG. 1 is a side perspective of one suitable embodiment of an absorbent article shown in the form of a training pant, the training pant having a mechanical fastening system fastened on one side of the training pant and unfastened on the opposite side thereof.

Referring now to the drawings and in particular to FIG. 1, one suitable embodiment of an absorbent article is illustrated in the form of a child's toilet training pant and is indicated in its entirety by the reference numeral 20. The term absorbent article generally refers to articles that may be placed against or in proximity to a body of a wearer to absorb and/or retain various exudates from the body. The absorbent training pant 20 may or may not be disposable. Disposable refers to articles that are intended to be discarded after a limited period of use instead of being laundered or otherwise conditioned for reuse. It is understood that the embodiments of the present disclosure are suitable for use with various other absorbent articles intended for personal wear, including but not limited to diapers, swim diapers, feminine hygiene products (e.g., sanitary napkins), incontinence products, medical garments, surgical pads and bandages, other personal care or health care garments, and the like without departing from the scope of the present disclosure.

By way of illustration only, various materials and methods for constructing training pant such as the pant 20 of the various aspects of the present disclosure are disclosed in PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al., which are incorporated herein by reference.

Figure 2:
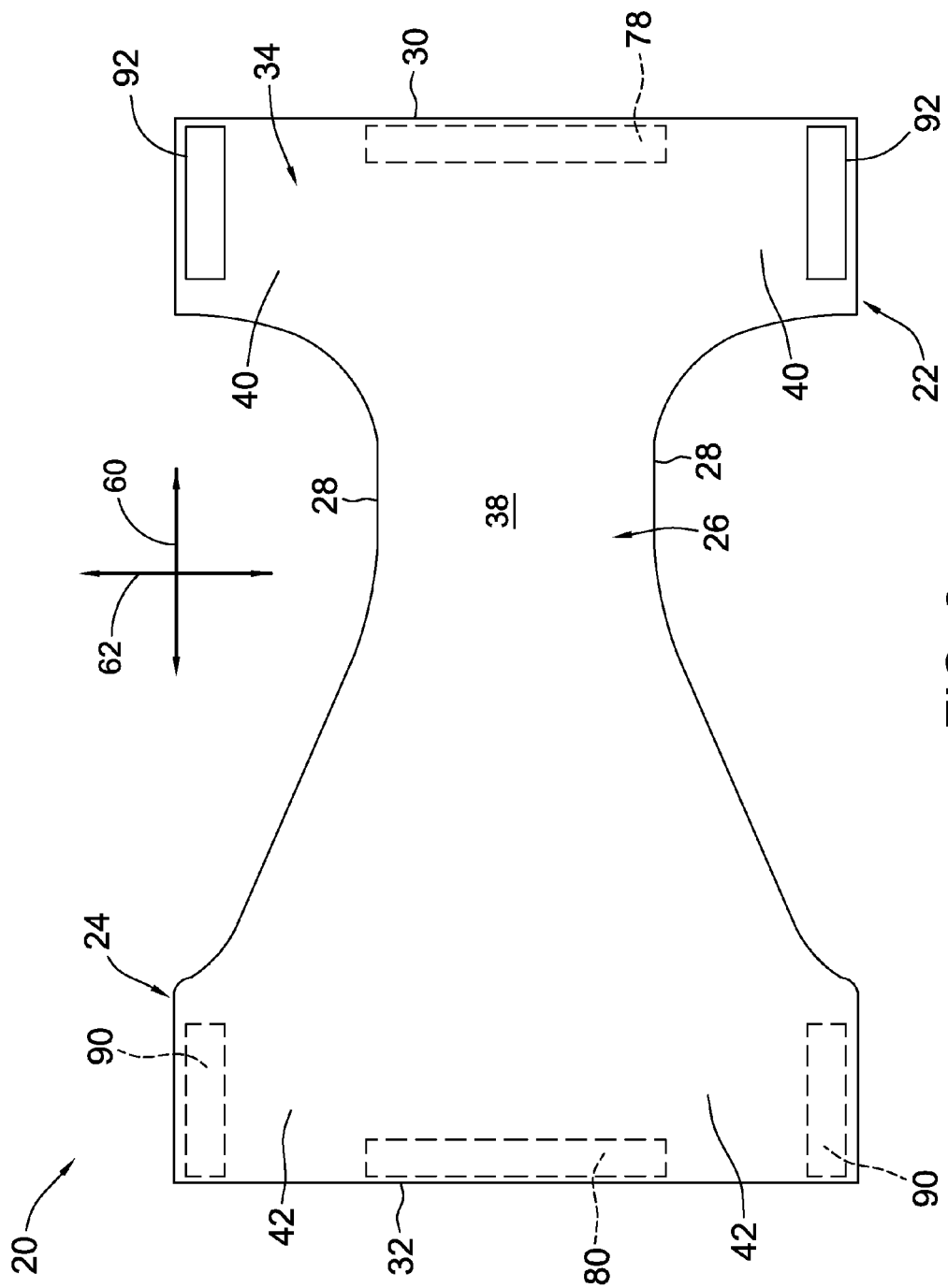
FIG. 2 illustrates a bottom plan view of the absorbent article of FIG. 1 with the training pant in an unfastened, unfolded and laid flat condition, and showing a surface of the training pant adapted to face away from the wearer during use.
Figure 3:
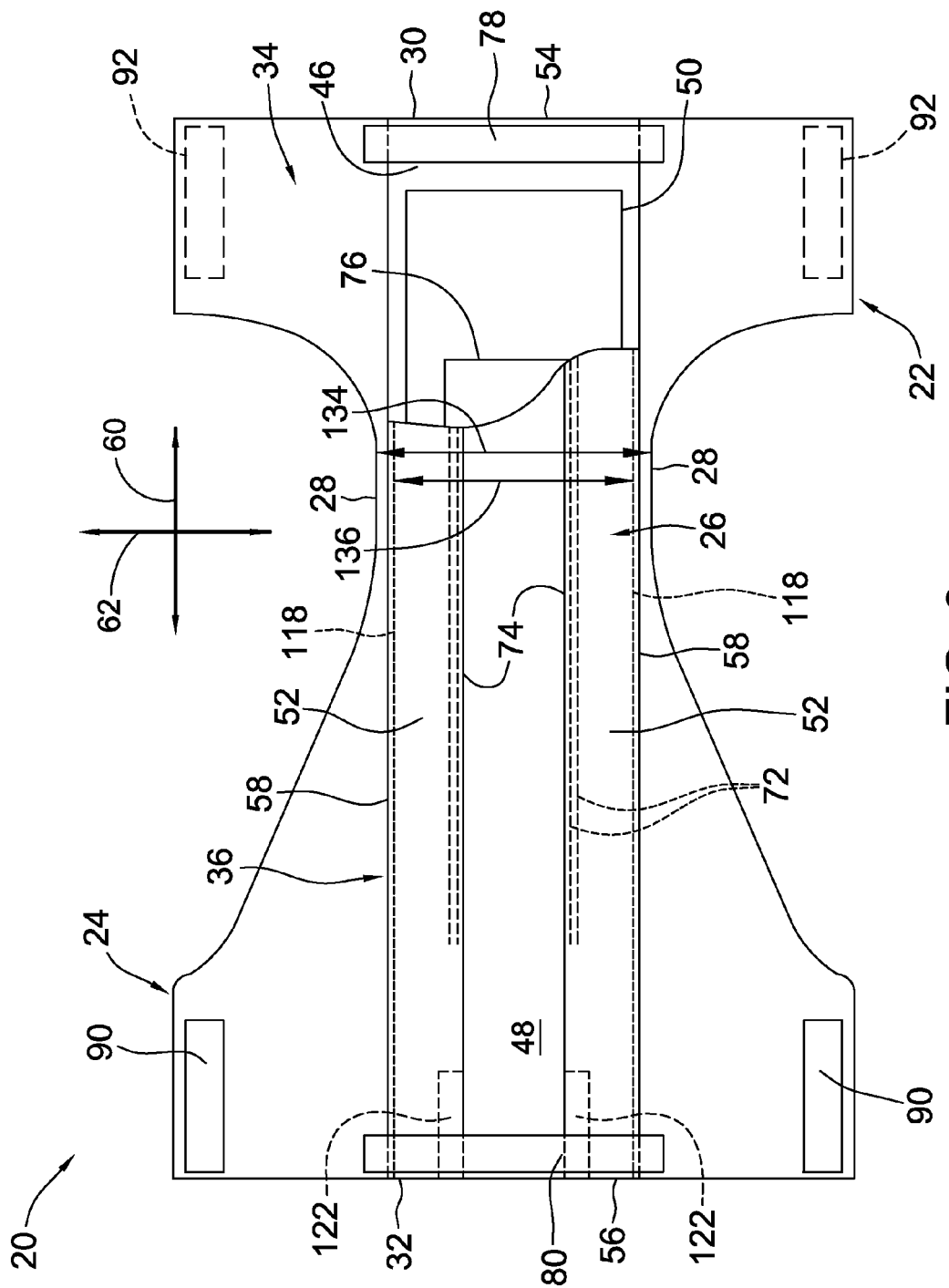
FIG. 3 illustrates a top plan view similar to FIG. 2 but showing a surface of the training pant adapted to face the wearer during use, portions of the training pant being cut away to show underlying features.

As seen in FIGS. 1-3, the training pant 20 has a front waist region 22, a back waist region 24, and a crotch region 26 disposed longitudinally between and interconnecting the front and back waist regions. The front waist region 22, the back waist region 24 and the crotch region 26 are indicated generally by the respective reference numbers. The training pant 20 also has a pair of laterally opposite side edges 28 and a pair of longitudinally opposite waist edges, respectively designated front waist edge 30 and back waist edge 32. The front waist region 22 is contiguous with the front waist edge 30, and the back waist region 24 is contiguous with the back waist edge 32.

With reference to FIGS. 2 and 3, the training pant 20 includes a chassis, indicated generally at 34, and an absorbent assembly, indicated generally at 36, attached to the chassis 34. Arrows 60 and 62 in FIGS. 2 and 3 depict the orientation of a longitudinal axis and a transverse or lateral axis, respectively, of the training pant 20. The illustrated absorbent assembly 36 extends longitudinally from the front waist region 22 through the crotch region 26 to the back waist region 24. While the illustrated absorbent assembly 36 is shown and described herein as extending from the crotch region 26 into both the front and back waist regions 22 and 24, it is contemplated that the absorbent assembly 36 may extend from the crotch region 26 into primarily the front waist region 22, or into primarily the back waist region 24, without departing from some aspects of this disclosure. Further, the absorbent assembly 36 may extend any suitable length along the crotch region 26 and/or into the front waist region 22 and/or the back waist region 24.

In the illustrated embodiment, the chassis 34 and the absorbent assembly 36 are formed separately from one another. It is contemplated, however, that the chassis 34 and the absorbent assembly 36 may be integrally formed with one another in some embodiments. It is further contemplated that in some suitable embodiments the absorbent assembly 36 can be disposable and the chassis 34 can be non-disposable. It is further contemplated that the absorbent assembly 36 can be configured to be inserted into conventional underwear. For example, the absorbent assembly 36 can include garment adhesive, as is known in the art, for adhering the absorbent assembly to the underwear. In such an embodiment, the underwear would define the chassis 34.

As seen in FIGS. 2 and 3, the chassis 34 includes a longitudinally extending central portion 38, a pair of laterally opposite front side portions 40 extending outward from the central portion 38 at the front waist region 22 (thereby forming transversely outer portions of the front waist region, and more broadly in part forming transversely opposite sides of the training pant), and a pair of laterally opposite back side portions 42 extending outward from the central portion at the back waist region 24 (thereby forming transversely outer portions of the back waist region, and together with the front side portions 40 further defining the sides of the pant). In the illustrated embodiment, the central portion 38 extends from the front waist region 22 through the crotch region 26 to the back waist region 24 of the training pant 20.

In one suitable embodiment and as seen in FIGS. 2 and 3, the front side portions 40, the back side portions 42, and the central portion 38 are formed from the same sheet of material. In other suitable embodiments, one or more of the front side portions 40, the back side portions 42, and/or the central portion 38 may be formed from two or more separate elements. For example, in one suitable embodiment, the front side portions 40 and/or the back side portions 42 can be formed separately from and attached to the central portion 38. It is contemplated that in some suitable embodiments, the back side portions, the front side portions, or the central portion 38 (at least in the crotch region 26 of the training pant 20) can be omitted. For example, in one such embodiment, the central portion 38 can be omitted from the region 26 of the training pant 20. The front side portions 40 and the back side portions 42 can then be formed from separate sheets of material (in which case the front side portions 40 and back side portions 42 are more accurately described as panels). For example, in the embodiment illustrated in FIG. 9, a training pant 420 includes front and back side panels 502, 504 formed separately from and secured to the absorbent assembly 36, described in more detail below. In such an embodiment, at least a portion of the crotch region 26 of the training pant 420 is free of the chassis.

The chassis 34 has a minimum width 134 taken along the lateral axis 62 of the training pant 20. In the illustrated embodiment of FIG. 3, the minimum width 134 is located along the central portion 38 (FIG. 2) of the chassis 34, and within the crotch region 26 of the training pant 20. The minimum width 134 of the illustrated chassis 34 generally corresponds to a portion of the training pant that is positioned between the legs of the wearer and covers the lower torso of the wearer, specifically the perineum region of the wearer.

The chassis 34 may comprise any suitable material including, for example and without limitation, a liquid permeable material that provides a generally cloth-like texture. The chassis 34 can be a single layer of material, or a multi-layered laminate structure. The chassis 34 or portions thereof may also be made of those materials of which the liquid permeable bodyside liner 48 is made. In other suitable embodiments, it is contemplated that the chassis 34 can be liquid impermeable. It is further contemplated that the chassis 34 can be vapor impermeable or vapor permeable (i.e., "breathable").

One suitable "breathable" material is composed of a microporous polymer film or a nonwoven fabric that has been coated or otherwise treated to impart a desired level of liquid impermeability.

It is also contemplated that the chassis 34 may be stretchable, and more suitably elastic. In particular, the chassis 34 is suitably stretchable and more suitably elastic in at least the transverse, or circumferential direction of the pant 20. In other embodiments, the chassis 34 may be stretchable, and more suitably elastic, in both the transverse and the longitudinal direction. It is contemplated that the chassis 34 can be stretchable in any suitable direction.

The absorbent training pant 20 and more specifically the chassis 34 may include a front waist elastic member 78, a rear waist elastic member 80, and/or leg elastic members (not shown), as are known to those skilled in the art. The waist elastic members 78, 80 can be attached to the inner surface of the chassis 34 (i.e., the surface of the chassis that faces the wearer when worn) or the outer surface of the chassis 34 (i.e., the surface of the chassis that faces away from the wearer). Likewise, the leg elastic members can be attached to the inner surface of the chassis 34 or the outer surface of the chassis 34 along the opposite side edges 28 and positioned in the crotch region 26 of the absorbent training pant 20. The leg elastic members can be longitudinally aligned along side edges 58 of the absorbent assembly 36, or the leg elastic members can be aligned with the opposite side edges 28 of the absorbent article.

While the training pant 20 of the illustrated embodiment has a pair of refastening seams 70 disposed on the side of the pant (one seam being illustrated in FIG. 1), it is understood that the seams can be located at any suitable location on the pant and that the seams can be permanently attached (e.g., by adhesive, ultrasonic bonding, pressure bonding, thermal bonding). Moreover, while the illustrated refastening seams 70 are defined by loop fastening components 90 (broadly, a "first fastening component") selectively engageable with hook fastening components 92 (broadly, a "second fastening component"), it is contemplated that any suitable refastenable fasteners can be used such as other types of mechanical fasteners, adhesive fasteners, cohesive fasteners.

Figure 4:
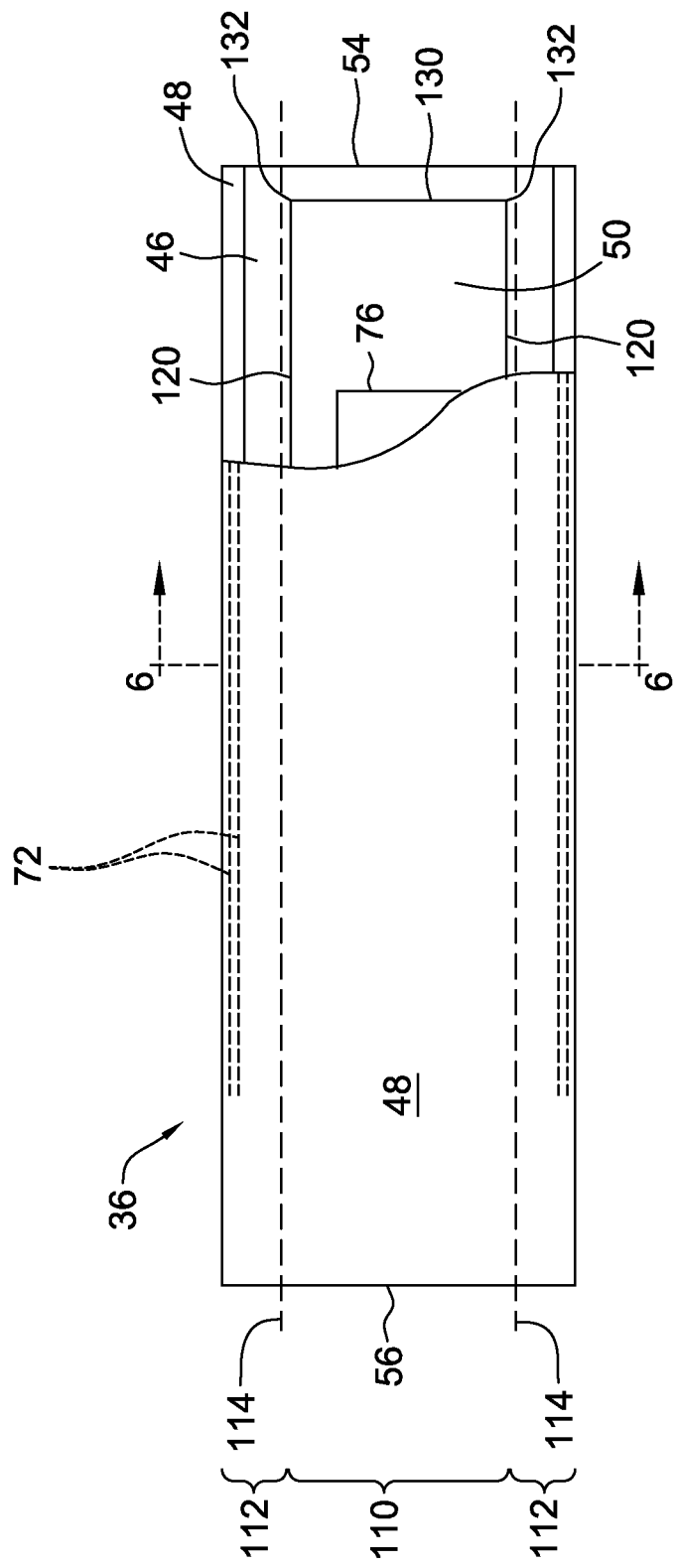
FIG. 4 is a top plan view of one suitable embodiment of an absorbent assembly suitable for use with the training pant of FIGS. 1-3 in an unfolded and laid flat configuration, portions of the absorbent assembly being cut away to show underlying features.

Referring to FIGS. 3 and 4, the absorbent assembly 36 of the illustrated embodiment is attached to the chassis 34 along at least the crotch region 26 of the absorbent training pant 20 by an adhesive, ultrasonic bonds, thermal bonds, pressure bonds, or the like. Suitable adhesives can be applied continuously or intermittently as beads, a spray, parallel swirls, or the like. Suitable ultrasonic bonds, pressure bonds, and/or thermal bonds can be formed continuously or intermittently along the absorbent assembly 36 to effect the attachment of the absorbent assembly 36 to the chassis 34. In the illustrated embodiment, the absorbent assembly 36 is permanently attached to the chassis 34. The term "permanently attached" is synonymous with terms such as "permanently joined," "permanently adhered," and "permanently bonded," and is intended herein to refer to an attachment that is generally not releasable without some damage or substantially reduced functionality of the components that are permanently attached. In another suitable embodiment, the absorbent assembly 36 is releasably attached to the chassis 34 by refastenable fasteners suitable for absorbent articles, such as adhesive fasteners, cohesive fasteners, mechanical fasteners (e.g., interlocking geometric shaped materials, such as hooks, loops, bulbs, mushrooms, arrowheads, balls on stems, male and female mating components, buckles, snaps) or the like.

While the absorbent assembly 36 illustrated in FIG. 3 is shown and described herein as being attached to the chassis 34 along the crotch region 26, it is contemplated that the absorbent assembly 36 may be attached to the chassis 34 along any one or more of the crotch region 26, the front waist region 22, and/or the back waist region 24, without departing from the scope of this disclosure. Further, the absorbent assembly 36 may be attached to the chassis 34 along any suitable length and/or area of the chassis 34.

As seen in FIGS. 3 and 4, the illustrated absorbent assembly 36 is generally rectangular in shape having a front end 54, a back end 56, and longitudinally extending side edges 58. The absorbent assembly 36 is illustrated in FIGS. 3 and 4 as having a rectangular shape, although it is contemplated that the absorbent assembly 36 may have other suitable shapes without departing from the scope of the present disclosure. In the illustrated embodiment, the front and back ends 54, 56 of the absorbent assembly 36 define respective portions of the front and back waist edges 30, 32 of the training pant 20. It is contemplated, however, that the front end 54 and/or back end 56 of the absorbent assembly 36 can be spaced inward from the front and back waist edges 30, 32 of the training pant 20. In such an embodiment, the front and back waist edges 30, 32 of the training pant 20 are defined solely by the chassis 34. As illustrated in FIG. 3, the side edges 58 of the absorbent assembly 36 can be spaced slightly inward from the side edges 28 of the absorbent training pant 20. In other embodiments (see, e.g., FIG. 9), the opposite side edges 58 of the absorbent assembly 36 can form portions of the side edges 28 of the absorbent training pant 20. It is further contemplated that the front end 54 and/or back end 56 of the absorbent assembly 36 can be folded over (in a direction away from the chassis 34) to create a pocket.

In one suitable embodiment, the absorbent assembly 36 comprises a liquid impermeable backsheet 46 and a bodyside liner 48 attached to the backsheet in a superposed relation by suitable means such as adhesives, ultrasonic bonds, pressure bonds, thermal bonds or other conventional techniques. An absorbent structure (or absorbent core) 50 is disposed between the backsheet 46 and the bodyside liner 48. A pair of containment flaps 52 is integrally formed from the absorbent assembly 36, as described in more detail below, for inhibiting the lateral flow of body exudates.

In one suitable embodiment, the backsheet comprises a material which is substantially liquid impermeable. The backsheet 46 can be a single layer of liquid impermeable material, or may comprise a multi-layered laminate structure in which at least one of the layers is liquid impermeable. Multiple layers of the backsheet 46 may be suitably joined together by an adhesive, ultrasonic bonds, pressure bonds, thermal bonds, or the like. Suitable adhesives can be applied continuously or intermittently as beads, a spray, parallel swirls, or the like.

The backsheet 46 can be both liquid and vapor impermeable, or, more suitably, it may be liquid impermeable and vapor permeable. The backsheet 46 can be manufactured from a thin plastic film, although other flexible liquid impermeable materials may also be used. The backsheet 46 prevents waste material from wetting articles, such as bed sheets and clothing, as well as the wearer and caregiver.

In one suitable embodiment, the liquid impermeable material can permit vapors to escape from the interior of the disposable absorbent article, while still preventing liquids from passing through the backsheet 46. One suitable "breathable" material is composed of a microporous polymer film or a nonwoven fabric that has been coated or otherwise treated to impart a desired level of liquid impermeability.

It is also contemplated that the backsheet 46 may comprise a liquid permeable material, or the backsheet 46 may be omitted from the absorbent assembly 36 altogether. In such embodiments, the chassis 34 suitably comprises a liquid impermeable material to provide a liquid barrier to body exudates. In one embodiment in which the backsheet 46 is omitted, the bodyside liner 48 is attached to the chassis 34 such that the absorbent structure 50 is disposed between the bodyside liner 48 and the inner surface of the chassis 34. In another suitable embodiment, both the absorbent structure 50 and the bodyside liner 48 are attached to the chassis 34.

It is also contemplated that the backsheet 46 may be stretchable, and more suitably elastic. In particular, the backsheet 46 is suitably stretchable and more suitably elastic in at least the transverse, or circumferential direction of the pant 20. In other embodiments the backsheet 46 may be stretchable, and more suitably elastic, in both the transverse and the longitudinal direction.

The bodyside liner 48 is suitably compliant, soft-feeling, and non-irritating to the wearer's skin. The bodyside liner 48 is also sufficiently liquid permeable to permit liquid body exudates to readily penetrate through its thickness to the absorbent structure 50. Further, the bodyside liner 48 can be less hydrophilic than the absorbent structure 50 to present a relatively dry surface to the wearer and permit liquid to readily penetrate through its thickness. The hydrophilic/hydrophobic properties can be varied across the length, width and/or depth of the bodyside liner 48 and absorbent structure 50 to achieve the desired rate of fluid intake and dryness.

A suitable bodyside liner 48 may be manufactured from a wide selection of web materials, such as porous foams, reticulated foams, apertured plastic films, woven and nonwoven webs, or a combination of any such materials. For example, the bodyside liner 48 may comprise a meltblown web, a spunbonded web, or a bonded-carded-web composed of natural fibers, synthetic fibers or combinations thereof. The bodyside liner 48 may be composed of a substantially hydrophobic material, and the hydrophobic material may optionally be treated with a surfactant or otherwise processed to impart a desired level of wettability and hydrophilicity. The surfactant can be applied by any conventional means, such as spraying, printing, brush coating or the like. The surfactant can be applied to the entire bodyside liner 48 or can be selectively applied to particular sections of the bodyside liner, such as the medial section along the longitudinal center line.

In some embodiments, a central zone 126 (FIG. 7) of the bodyside liner 48 (e.g., the portion of the bodyside liner 48 that is coextensive with and/or attached to the absorbent structure 50) and/or the portions of the bodyside liner 48 from which the containment flaps 52 are formed (referred to as lateral outer zones 128 (FIG. 7) of the bodyside liner 48) may be treated or otherwise coated to impart a desired level of liquid permeability or impermeability in the respective zones 126, 128. In one embodiment, the lateral outer zones 128 of the body side liner 48 are treated or coated such that the lateral outer zones 128 are less liquid-permeable than the central zone 126. In such embodiments, the backsheet 46 may extend only partially into the containment flaps 52, or, in some embodiments, not at all, as the bodyside liner 48 is sufficiently liquid impermeable along the containment flaps 52 to provide a barrier to the transverse flow of body exudates.

In one particularly suitable embodiment, the lateral outer zones 128 have a hydrostatic head greater than the hydrostatic head of the central zone 126. More specifically, the ratio of the hydrostatic head of the lateral outer zones 128 to the hydrostatic head of the central zone 126 is at least about 2, and more suitably, at least about 5. In one suitable example, the lateral outer zone has a hydrostatic head greater than about 40 cm, and more suitable, greater than about 100 cm.

Hydrostatic head is a measure of the liquid barrier properties of a fabric. Hydrostatic head refers to the height of water (in centimeters) which the fabric will support before a predetermined amount of liquid passes through. A fabric with a higher hydrostatic head reading indicates it has a greater barrier to liquid penetration than a fabric with a lower hydrostatic head. Materials having a suitable hydrostatic head, as well as methods of making such materials, are described in U.S. Pat. No. 5,482,765 issued Jan. 9, 1996 to Bradley et al.; U.S. Pat. No. 5,492,751 issued Feb. 20, 1996 to Butt, Sr. et al.; and U.S. Pat. No. 6,822,136 issued Nov. 23, 2004 to Niemeyer et al., which are incorporated herein by reference.

In yet other embodiments, the bodyside liner 48 may have a gradient of permeability, with greater permeability toward the central zone 126 of the liner 48. More particularly, the bodyside liner 48 may have greater permeability closer to the crotch region 26 of the absorbent training pant 20, and less permeability toward the free edge 74 of the containment flaps 52. Desired levels of liquid-permeability in the bodyside liner 48 can be rendered by zone-treating or otherwise coating selective portions of the bodyside liner 48 with surfactants, using desired liquid-permeable materials, or inducing permeability through partial or selective dispersibility.

In other embodiments, the bodyside liner 48 may be formed from different, discrete materials to obtain a desired level of liquid permeability or impermeability in the respective zones 126, 128. For example, in the alternative embodiment of FIGS. 8A and 8B, the absorbent assembly 236 includes a bodyside liner 304 comprising a liquid permeable central liner 306 and two liquid impermeable outer liners 308, described in more detail below.

The bodyside liner 48 may also be stretchable, and more suitably it may be elastomeric. Suitable elastomeric materials for construction of the bodyside liner 48 can include elastic strands, LYCRA elastics, cast or blown elastic films, nonwoven elastic webs, meltblown or spunbond elastomeric fibrous webs, as well as combinations thereof. Examples of suitable elastomeric materials include KRATON elastomers, HYTREL elastomers, ESTANE elastomeric polyurethanes (available from Noveon of Cleveland, Ohio), or PEBAX elastomers. The bodyside liner 48 can also be made from extensible materials as are described in U.S. patent application Ser. No. 09/563,417 filed on May 3, 2000 by Roessler et al. or from biaxially stretchable materials as are described in U.S. patent application Ser. No. 09/698,512 filed on Oct. 27, 2000 by Vukos et al., both references which are hereby incorporated by reference.

The absorbent structure 50 is disposed between the backsheet 46 and the bodyside liner 48 and has longitudinally opposite ends 130 (FIG. 4) and laterally opposite side edges 120 that meet at respective corner regions 132 of the absorbent structure 50. As used herein, the corner regions 132 of the absorbent structure 50 refer generally to those regions at which the edge margin of the absorbent structure 50 transitions from a longitudinal end to an adjacent lateral side edge. For example, in the illustrated embodiment, the longitudinal ends 130 of the absorbent structure 50 intersect (e.g., at a right angle) the lateral side edges 120 such that the corner regions 132 of the absorbent structure 50 are generally a defined point. However, it is contemplated that the corner regions 132 may be rounded, e.g., where the absorbent structure 50 is curved to define a rounded transition from the longitudinal ends 130 to adjacent lateral side edges 120, and remain within the meaning of the term corner region as used herein as well as within the scope of this disclosure. As such, the absorbent structure 50 of the illustrated embodiment has four defined corner regions 132, two of which are laterally spaced from each other at the front waist region 22 of the pant 20 (FIG. 3) and the other two of which are laterally spaced from each other at the back waist region 24 of the pant.

Figure 5:
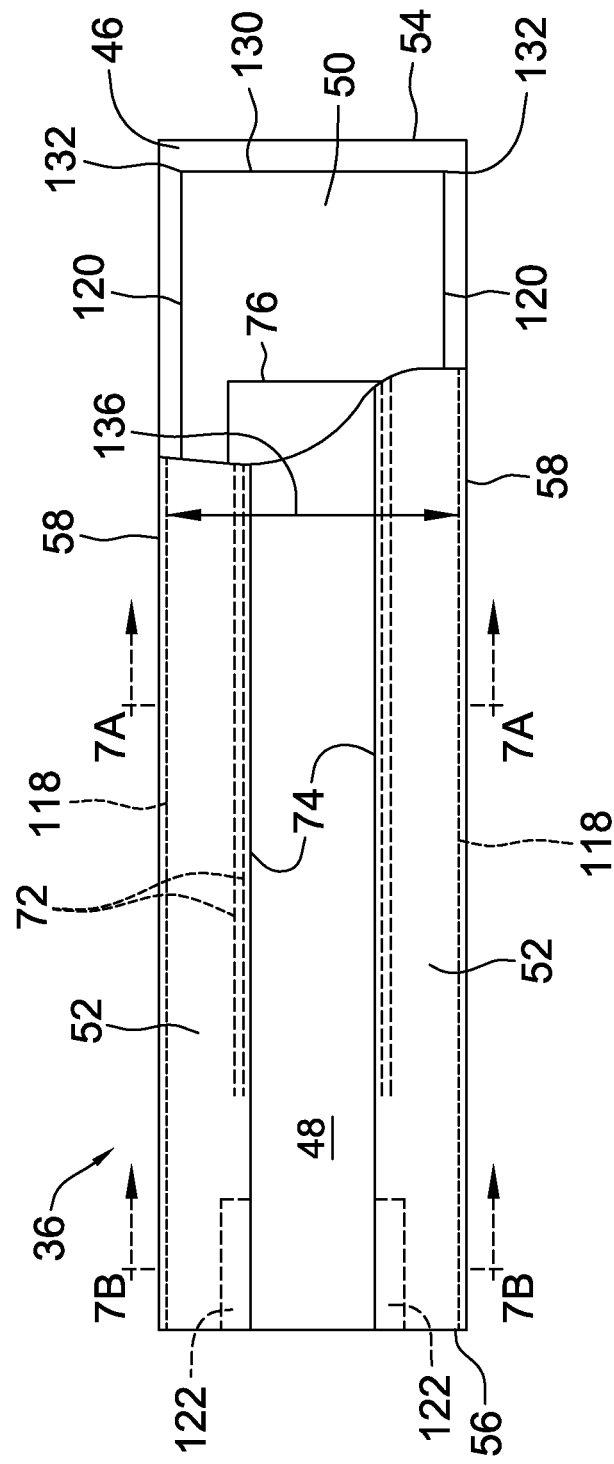
FIG. 5 is a top plan view of the absorbent assembly of FIG. 4 in a folded and laid flat configuration, portions of the absorbent assembly being cut away to show underlying features.

As seen in FIGS. 4 and 5, the illustrated absorbent structure 50 is generally rectangular. It is contemplated, however, that the absorbent structure 50 can have any suitable shape and size. For example, the absorbent structure 50 can include arcuate leg cutouts (e.g., by die cutting the absorbent structure) in the crotch region 26 of the training pant 20.

While the illustrated absorbent structure 50 is shown and described herein as extending from the crotch region 26 into both the front and back waist regions 22 and 24, it is contemplated that the absorbent structure may extend from the crotch region 26 into only the front waist region 22, or only the back waist region 24, without departing from the scope of this disclosure.

The absorbent structure 50 is suitably compressible, conformable, non-irritating to a wearer's skin, and capable of absorbing and retaining liquids and certain body wastes. For example, the absorbent structure 50 may comprise cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent structure comprises a matrix of cellulosic fluff and superabsorbent hydrogel-forming particles. The cellulosic fluff may include a blend of wood pulp fluff. Suitable types of fluff include, for example, fluff pulp commercially available from Weyerhaeuser Company under the designation FR416 (7.5 percent Moisture) and CF416 (7.5 percent Moisture). Weyerhaeuser Company has offices in Federal Way, Wash. U.S.A.

The materials may be formed into a web structure by employing various conventional methods and techniques. For example, the absorbent structure 50 may be formed by a dry-forming technique, an air forming technique, a wet-forming technique, a foam-forming technique, or the like, as well as combinations thereof. Methods and apparatus for carrying out such techniques are well known in the art. Furthermore, the absorbent structure 50 may itself encompass multiple layers in a Z-direction (e.g., thickness) of the absorbent structure 50. Such multiple layers may take advantage of differences in absorbent capacity, such as by placing a lower absorbent capacity material layer closer to the liner 48 and a higher absorbent capacity material closer to the backsheet 46. Likewise, discrete portions of a single-layered absorbent structure may encompass higher capacity absorbents, and other discrete portions of the structure may encompass lower capacity absorbents.

Superabsorbent material is suitably present in the absorbent structure 50 in an amount of from about 0 to about 100 weight percent based on total weight of the absorbent structure 50. The absorbent structure 50 may suitably have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and preferably is capable of absorbing more than about 25 times its weight in liquid. Suitable superabsorbent materials are readily available from various suppliers. For example, Hysorb T 9700 superabsorbent, which is commercially available from BASF of Ludwigshafen, Germany, or Favor SXM 5600 superabsorbent, which is commercially available from Evonik of Essen, Germany.

The absorbent structure 50 may alternatively comprise a coform material. The term "coform material" generally refers to composite materials comprising a mixture or stabilized matrix of thermoplastic fibers and a second non-thermoplastic material. As an example, coform materials are made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein by reference.

In one suitable embodiment, the absorbent structure 50 is stretchable so as not to inhibit the stretchability of other components to which the absorbent structure may be adhered, such as the backsheet 46 and bodyside liner 48. After being formed or cut to a desired shape, the absorbent structure 50 may be wrapped or encompassed by a suitable wrap (not shown) that aids in maintaining the integrity and shape of the absorbent structure.

The absorbent assembly 36 is configured to contain and/or absorb exudates discharged from the wearer. For example, the containment flaps 52 are configured to provide a barrier to the transverse flow of body exudates. A flap elastic member 72 (FIG. 3) may be operatively joined with each containment flap 52, as described in more detail below. The elasticized containment flaps 52 define a partially unattached, or free, edge 74 (FIG. 3) which assumes an upright configuration in at least the crotch region 26 of the absorbent training pant 20 to form a seal against the wearer's body during use. In one suitable embodiment, the containment flaps 52 can be located along the side edges 28 of the training pant 20, and can extend longitudinally along the entire length of the absorbent assembly 36 or may only extend partially along the length of the absorbent assembly 36.

In the illustrated embodiment, the absorbent assembly 36 also includes a surge management layer 76 located adjacent the absorbent structure 50 (e.g., between the absorbent structure 50 and the liner 48). The surge management layer 76 helps to decelerate and diffuse surges or gushes of liquid that may be rapidly introduced into the absorbent structure 50 of the training pant 20 by the wearer. Desirably, the surge management layer 76 can rapidly accept and temporarily hold the liquid prior to releasing the liquid into the storage or retention portions of the absorbent structure 50. Examples of suitable surge management layers are described in U.S. Pat. No. 5,486,166 issued Jan. 23, 1996 to Bishop et al.; U.S. Pat. No. 5,490,846 issued Feb. 13, 1996 to Ellis et al.; and U.S. Pat. No. 5,820,973 issued Oct. 13, 1998 to Dodge, II et al., the entire disclosures of which are hereby incorporated by reference herein.

Figure 6:
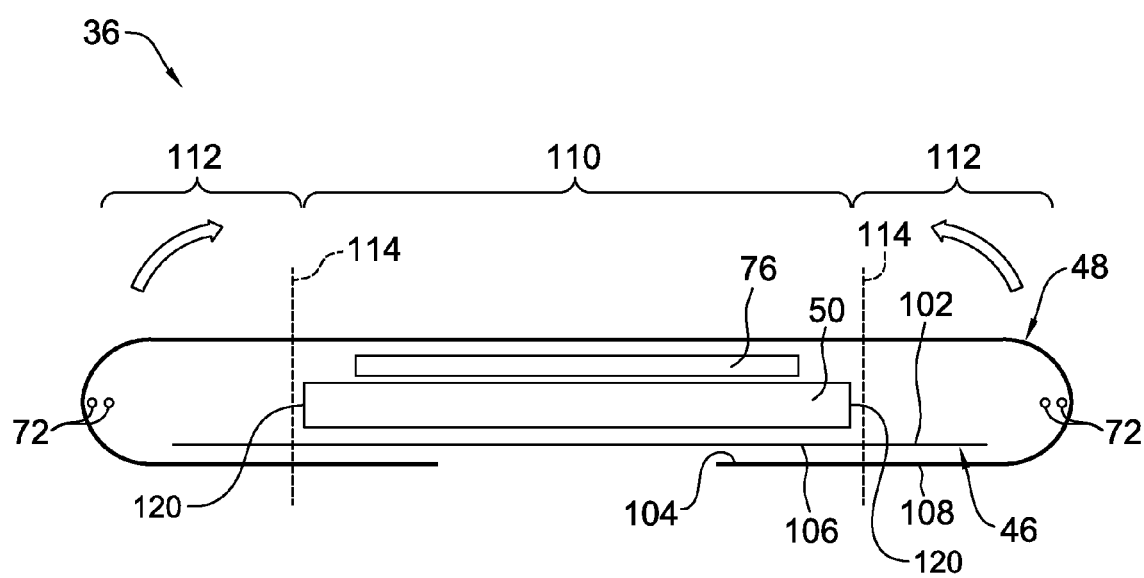
FIG. 6 is a cross-section of the absorbent assembly of FIG. 4 taken along line 6-6.

With particular reference now to FIGS. 3-7B, the absorbent assembly 36 will be described in greater detail. FIG. 4 is a top plan view of the absorbent assembly 36 in an unfolded, laid flat configuration in which the containment flaps 52 have not been fully formed. Portions of the absorbent assembly 36 are cut away in FIG. 4 to show underlying features. FIG. 6 is a cross-section of the absorbent assembly 36 taken along line 6-6 of FIG. 4. The backsheet 46 and the bodyside liner 48 each include an inward-facing side 102, 104 (i.e., the side that faces the interior of the absorbent assembly 36), and an outward-facing side 106, 108 (i.e., the side that faces away from the interior of the absorbent assembly 36), respectively.

As shown in FIGS. 4-7B, the bodyside liner 48 extends around the absorbent structure 50 and the backsheet 46 such that the inward-facing side 104 of the bodyside liner 48 overlaps the outward-facing side 106 of the backsheet 46. The absorbent structure 50 and the backsheet 46 are thereby enclosed within the bodyside liner 48. In the illustrated embodiment, the backsheet 46 is partially enclosed by the bodyside liner 48, although it is contemplated that the backsheet 46 may be fully enclosed by the bodyside liner. The bodyside liner 48 is attached to the backsheet 46 using suitable means such as adhesives, ultrasonic bonds, pressure bonds, thermal bonds or other conventional techniques. The bodyside liner 48 can be attached to the backsheet 46 along the inward-facing side 102 and/or the outward-facing side 106 of the backsheet 46. In one suitable embodiment, the bodyside liner 48 is attached to the backsheet 46 along the portion of the bodyside liner 48 that overlaps the outward-facing side 106 of the backsheet 46.

The absorbent structure 50 is disposed between the bodyside liner 48 and the backsheet 46 along a central region 110 of the absorbent assembly 36. In one suitable embodiment, the absorbent structure 50 is attached the bodyside liner 48 and/or the backsheet 46 using suitable means such as adhesives, ultrasonic bonds, pressure bonds, thermal bonds or other conventional techniques. In the illustrated embodiment, the absorbent structure 50 is attached to both the bodyside liner 48 and the backsheet 46. It is understood, however, that the absorbent structure 50 does not need to be bonded to either the bodyside liner 48 or the backsheet 46.

The absorbent assembly 36 illustrated in FIG. 4 also includes lateral outer regions 112 extending laterally outward from the central region 110 from which the containment flaps 52 are formed. Flap elastic members 72 are positioned within each lateral outer region 112 such that the flap elastic members 72 are positioned within the containment flaps 52 once formed. The containment flaps 52 are formed by folding the lateral outer portions 112 laterally inwards as indicated by the arrows in FIG. 6 about longitudinal fold lines 114, which is illustrated in FIG. 4, into face-to-face contact with the outward-facing side 108 of the bodyside liner 48 along the central region 110 of the absorbent assembly 36.

The lateral outer regions 112 are suitably attached to the bodyside liner 48 by an adhesive seam 116 extending longitudinally along the absorbent assembly 36, thereby forming a fixed edge 118 (FIGS. 3, 7A, and 7B) of each containment flap 52. Suitable adhesives can be applied continuously or intermittently to the bodyside liner 48 as beads, a spray, parallel swirls, or the like. The adhesive seams 116 can extend any suitable length along the crotch region 26 of the pant 20. Further, it is contemplated that the adhesive seams 116 may extend into the front waist region 22 and/or the back waist region 24, and may even extend to the ends 54 and/or 56 of the absorbent assembly 36. In the illustrated embodiment, the adhesive seams 116 are aligned with laterally opposing side edges 120 of the absorbent structure 50.

A portion of the lateral outer regions 112 are left unattached to the bodyside liner 48, at least along a portion of the crotch region 26, to form the free edge 74 of the containment flaps 52. The free edge 74 of the containment flaps 52 is disposed opposite the fixed edge 118, and is configured to assume an upright configuration in at least the crotch region 26 of the absorbent training pant 20. More specifically, the flap elastic members 72 are positioned proximate the free edge 74 such that when a tensile force is applied to the flap elastic members 72, the free edges 74 of the containment flaps 52 assume an upright configuration to form a seal against the wearer's body during use.

The flap elastic members 72 may be formed from the same elastic materials as the waist elastic members 78, 80 and/or the leg elastic members, including sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate.

The flap elastic members 72 can extend any suitable length along the containment flaps 52. In the illustrated embodiment, the flap elastic members 72 extend less than the full length of the containment flaps 52. In one suitable embodiment, the flap elastic members 72 extend along the containment flaps 52 only within the crotch region 26 of the training pant 20. In another suitable embodiment, the flap elastic members 72 are generally coextensive with the absorbent structure 50. That is, in one embodiment, the flap elastic members 72 within the containment flaps 52 extend the length of the absorbent structure 50. It is understood, however, that the flap elastic members 72 can extend any suitable length along the containment flaps 52 including, for example, the full length of the containment flaps 52. In one suitable embodiment, for example, the flap elastic members 72 can extend into the flap attachment zones 122, described below with reference to FIG. 3.

The flap elastic members 72 can include active portions (i.e., portions of the flap elastic member 72 that are elastic) and inactive portions (i.e., portions of the flap elastic member 72 that are non-elastic). Portions of the flap elastic members 72 can be rendered inactive (i.e., non-elastic) by, for example, chopping or otherwise "deadening" the flap elastic members 72 along a desired inactive portion. The flap elastic members 72 can include any suitable number of active and inactive portions having any suitable dimension and configuration. In one suitable embodiment, for example, longitudinally opposing ends of the flap elastic members 72 can extend into the flap attachment zones 122 (FIG. 3), and can be rendered inactive within the flap attachment zones 122.

Figure 7A:
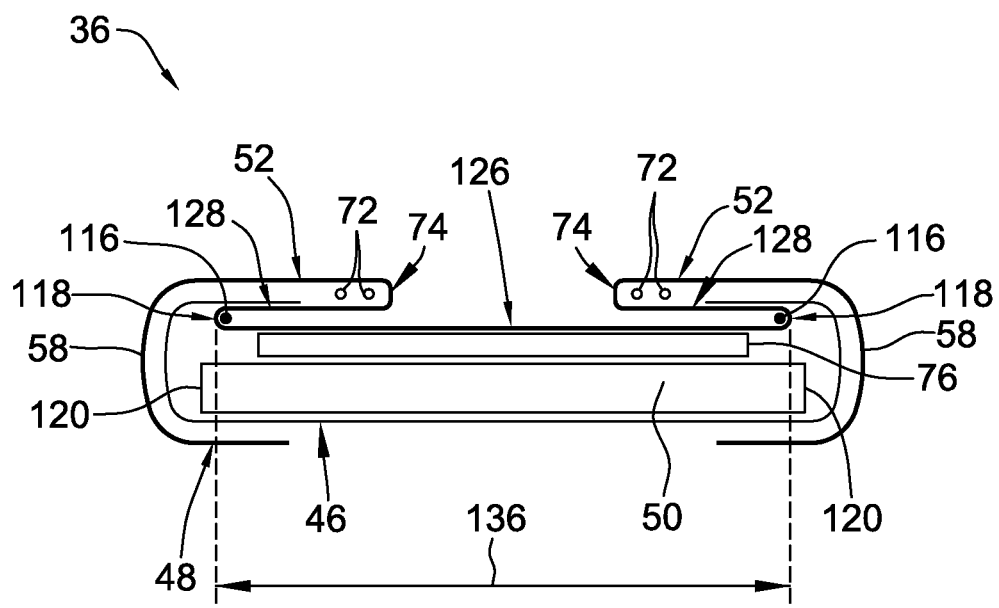
FIG. 7A is a cross-section of the absorbent assembly of FIG. 5 taken along line 7A-7A.
Figure 7B:
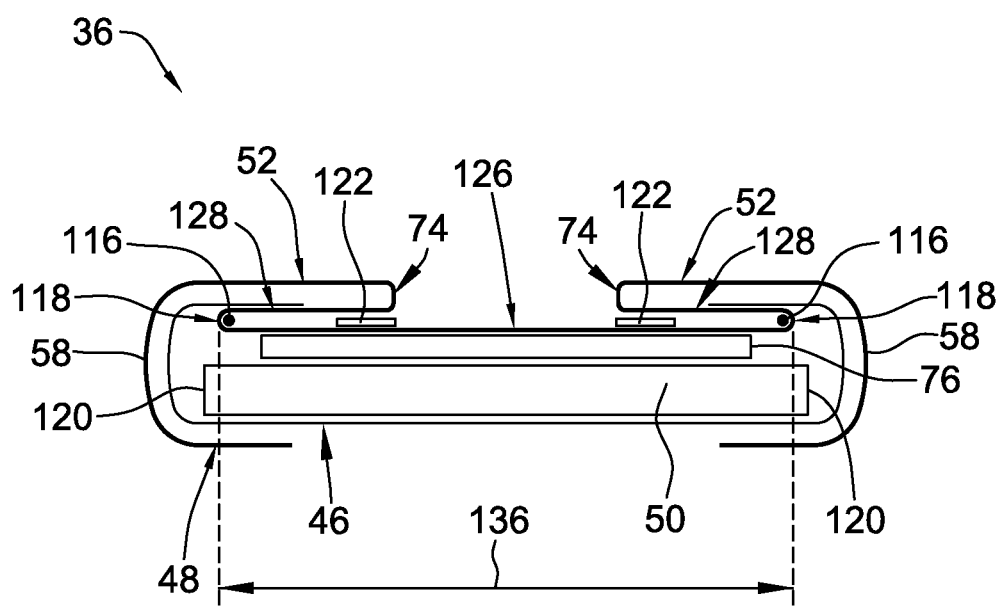
FIG. 7B is a cross-section of the absorbent assembly of FIG. 5 taken along line 7B-7B.

As shown in FIGS. 7A and 7B, when the containment flaps 52 are fully formed, the backsheet 46 is enclosed by the bodyside liner 48 within the containment flaps 52. More specifically, the containment flaps 52 comprise a portion of the backsheet 46 interposed between two layers of the bodyside liner 48. The backsheet 46 extends into the containment flaps 52 from the fixed edge 118 of a respective containment flap 52 towards the free edge 74 of the containment flaps. In the illustrated embodiment, the backsheet 46 suitably extends at least partially into the containment flaps 52 to provide a liquid impermeable layer within the containment flap 52. In the illustrated embodiment, the backsheet 46 extends only partially into the containment flap 52, although it is contemplated that the backsheet 46 may extend the entire length of the containment flap 52 to the free edge 74, or the backsheet 46 may not extend into the containment flap 52 at all.

The backsheet 46 can be suitably attached to the bodyside liner 48 and/or the absorbent structure 50 along the inward-facing side 102 and/or the outward-facing side 106 of the backsheet 46 by an adhesive, ultrasonic bonds, pressure bonds, thermal bonds, or the like. Suitable adhesives can be applied continuously or intermittently as beads, a spray, parallel swirls, or the like. In one suitable embodiment, the backsheet 46 is attached to the bodyside liner 48 within the containment flaps 52. More specifically, the outward-facing side 106 of the backsheet 46 is attached to the inward-facing side 104 of the bodyside liner 48 within the containment flaps 52. Alternatively, the inward-facing side 102 of the backsheet 46 is attached to the outward-facing side 108 of the bodyside liner 48 within the containment flaps 52.

In the illustrated embodiment, the backsheet 46 extends from within one containment flap 52, around the absorbent structure 50, and into the other containment flap 52, thereby forming a continuous liquid-impermeable barrier around the absorbent assembly 36. In some embodiments, it is contemplated that the backsheet 46 does not extend around the absorbent structure 50, and instead comprises segmented or discrete sheets of liquid impermeable material attached to the bodyside liner 48 within and/or proximate the containment flaps 52 such that the backsheet 46 forms a liquid impermeable barrier within the containment flaps 52. In such embodiments, the chassis 34 may suitably be formed of a liquid impermeable material to provide a liquid impermeable barrier between the absorbent structure 50 and the garment facing side of the pant 20.

As shown in FIGS. 3, 7A, and 7B, the fixed edges 118 of the containment flaps 52 are separated by a lateral distance 136. In the illustrated embodiment, the containment flaps 52 and the fixed edges 118 of the containment flaps 52 are substantially parallel to one another. As a result, the lateral distance 136 between the fixed edges 118 is substantially the same along the length of the containment flaps 52. In the illustrated embodiment, the fixed edges 118 of the containment flaps 52 are offset from the side edges 58 of the absorbent assembly 36. In some embodiments, the fixed edges 118 of the containment flaps 52 may be formed proximate the side edges 58 of the absorbent assembly 36 such that the containment flaps 52 are disposed on and/or aligned with the side edges 58 of the absorbent assembly 36. In such embodiments, the difference between the lateral distance 136 and the overall width of the absorbent assembly 36 is substantially equal to the width of the containment flaps 52.

In addition to the adhesive seam 116, the containment flaps 52 may be attached to the bodyside liner 48 along end portions of the containment flaps 52. In the illustrated embodiment, the containment flaps 52 are attached to the bodyside liner 48 within the front waist region 22 and the back waist region 24 to define flap attachment zones 122 (FIGS. 3 and 5). For example, the flap attachment zones 122 may be formed within the front waist region 22 and/or the back waist region 24 to enable the waist edges 30, 32 to form a better seal around the wearer's waist. The flap attachment zones 122 suitably extend to the ends 54, 56 of the absorbent assembly 36, and may extend through the front waist region 22 and/or the back waist region 24 and into the crotch region 26 of the absorbent training pant 20. In another embodiment, the flap attachment zones 122 may extend from the ends 54, 56 of the absorbent assembly 36 and only partially through the front waist region 22 and/or the back waist region 24.

Figure 8A:
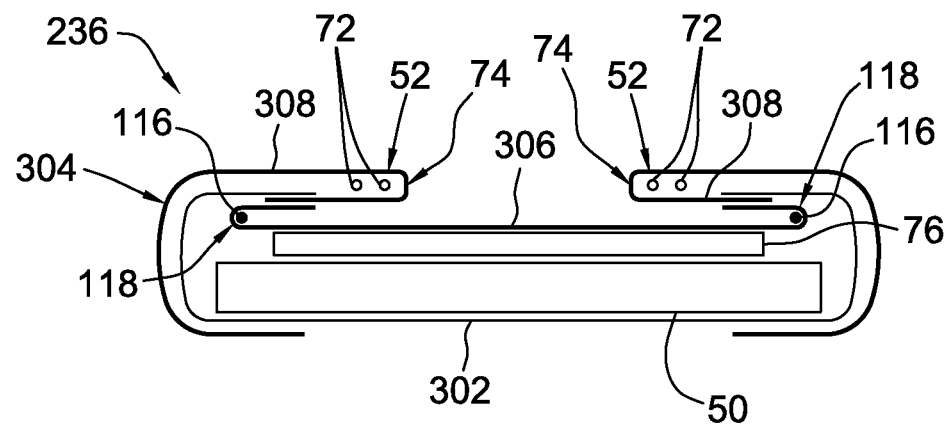
FIG. 8A is a cross-section of another suitable embodiment of an absorbent assembly for use with the training pant of FIGS. 1-3 taken through a crotch region of the absorbent assembly.
Figure 8B:
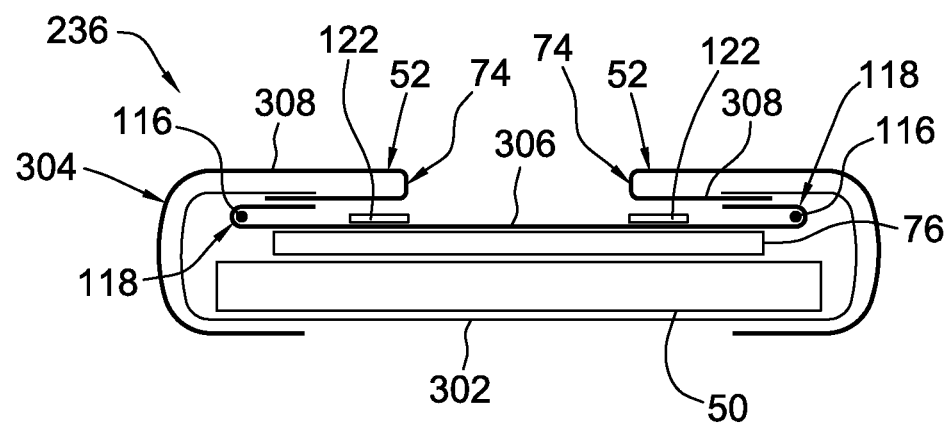
FIG. 8B is a cross-section of the embodiment of FIG. 8A taken through a back waist region of the absorbent assembly.

FIGS. 8A and 8B illustrate another suitable embodiment of an absorbent assembly 236 suitable for use with the training pant 20 of FIGS. 1-3. The absorbent assembly 236 is substantially similar to the absorbent assembly 36 described above. More specifically, the absorbent assembly 236 is attached to a chassis (not shown in FIGS. 8A and 8B) and extends longitudinally from the front waist region 22 through the crotch region 26 to the back waist region 24 of the training pant 20. As with the absorbent assembly 36, it is contemplated that the absorbent assembly 236 may extend from the crotch region 26 into only the front waist region 22, or only the back waist region 24, without departing from the scope of this disclosure. Further, the absorbent assembly 236 may extend any suitable length along the crotch region 26 and/or into the front waist region 22 and/or the back waist region 24.

The illustrated absorbent assembly 236 is generally rectangular in shape having a front end, a back end and longitudinally extending side edges. While the absorbent assembly 236 is illustrated in FIGS. 8A and 8B as having a rectangular shape, it is contemplated that the absorbent assembly 236 may have other suitable shapes without departing from the scope of the present disclosure.

In one suitable embodiment, the absorbent assembly 236 comprises a liquid impermeable backsheet 302 and a bodyside liner 304 attached to the backsheet 302 in a superposed relation by suitable means such as adhesives, ultrasonic bonds, pressure bonds, thermal bonds or other conventional techniques. An absorbent structure (or absorbent core) 50 is disposed between the backsheet 302 and the bodyside liner 304.

A pair of containment flaps 52 is integrally formed from the absorbent assembly 236 in the same manner as described above with reference to FIGS. 5-7B. More specifically, lateral outer regions of the absorbent assembly 236 are suitably attached to the bodyside liner 304 by an adhesive seam 116 extending longitudinally along the absorbent assembly 236, thereby forming a fixed edge 118 of each containment flap 52.

As with the absorbent assembly 36, a portion of containment flaps 52 are left unattached to the bodyside liner 304, at least along a portion of the crotch region 26, to form free edges 74 of the containment flaps 52. The free edge 74 of the containment flaps 52 is disposed opposite the fixed edge 118, and is configured to assume an upright configuration in at least the crotch region 26 of the absorbent training pant 20. More specifically, flap elastic members 72 are positioned proximate the free edge 74 such that when a tensile force is applied to the flap elastic members 72, the free edges 74 of the containment flaps 52 assume an upright configuration to form a seal against the wearer's body during use.

The backsheet 302 may comprise the same materials and have the same configuration as the backsheet 46 described above with reference to FIGS. 3-7B. In the embodiment illustrated in FIGS. 8A and 8B, the backsheet 302 may suitably comprise a liquid permeable material, or may suitably be omitted from the absorbent assembly 236 altogether as a result of the configuration of the bodyside liner 304.

The absorbent structure 50 may comprise the same materials and have the same configuration as the absorbent structure 50 described above with reference to FIGS. 3-7B.

Similar to the absorbent assembly 36, the absorbent assembly 236 includes a surge management layer 76 located adjacent the absorbent structure 50 (e.g., between the absorbent structure 50 and the bodyside liner 304) to help decelerate and diffuse surges or gushes of liquid that may be rapidly introduced into the absorbent structure 50 of the training pant 20 by the wearer.

The absorbent assembly 236 differs from the absorbent assembly 36 in that the bodyside liner 304 of the absorbent assembly 236 comprises a liquid permeable central liner 306 and two liquid impermeable outer liners 308 attached to laterally opposing sides of the central liner 306. In the embodiment of FIGS. 8A and 8B, the containment flaps 52 are suitably formed from the liquid impermeable outer liners 308. The liquid permeable central liner 306 and the liquid impermeable outer liners 308 are suitably compliant, soft-feeling, and non-irritating to the wearer's skin. The central liner 306 is sufficiently liquid permeable to permit liquid body exudates to readily penetrate through its thickness to the absorbent structure 50.

The liquid impermeable outer liners 308 suitably comprise a material which is substantially liquid impermeable, yet is suitably compliant, soft-feeling, and non-irritating to the wearer's skin. One particularly suitable material for the outer liners 308 includes a spun-bonded/meltblown/spun-bonded (S/M/S) laminate. Other suitable materials for the outer liners 308, and methods of making such materials, are described in U.S. Pat. No. 5,492,751 issued Feb. 20, 1996 to Butt, Sr. et al., which is incorporated herein by reference.

Because the containment flaps 52 of the absorbent assembly 236 are formed from the liquid impermeable outer liners 308, the backsheet 302 does not need to extend into the containment flaps 52 to the same extent as embodiments in which the containment flaps 52 are formed from a liquid permeable bodyside liner. It is further contemplated that the backsheet 302 may be omitted from the absorbent assembly 236 altogether.

Figure 9:
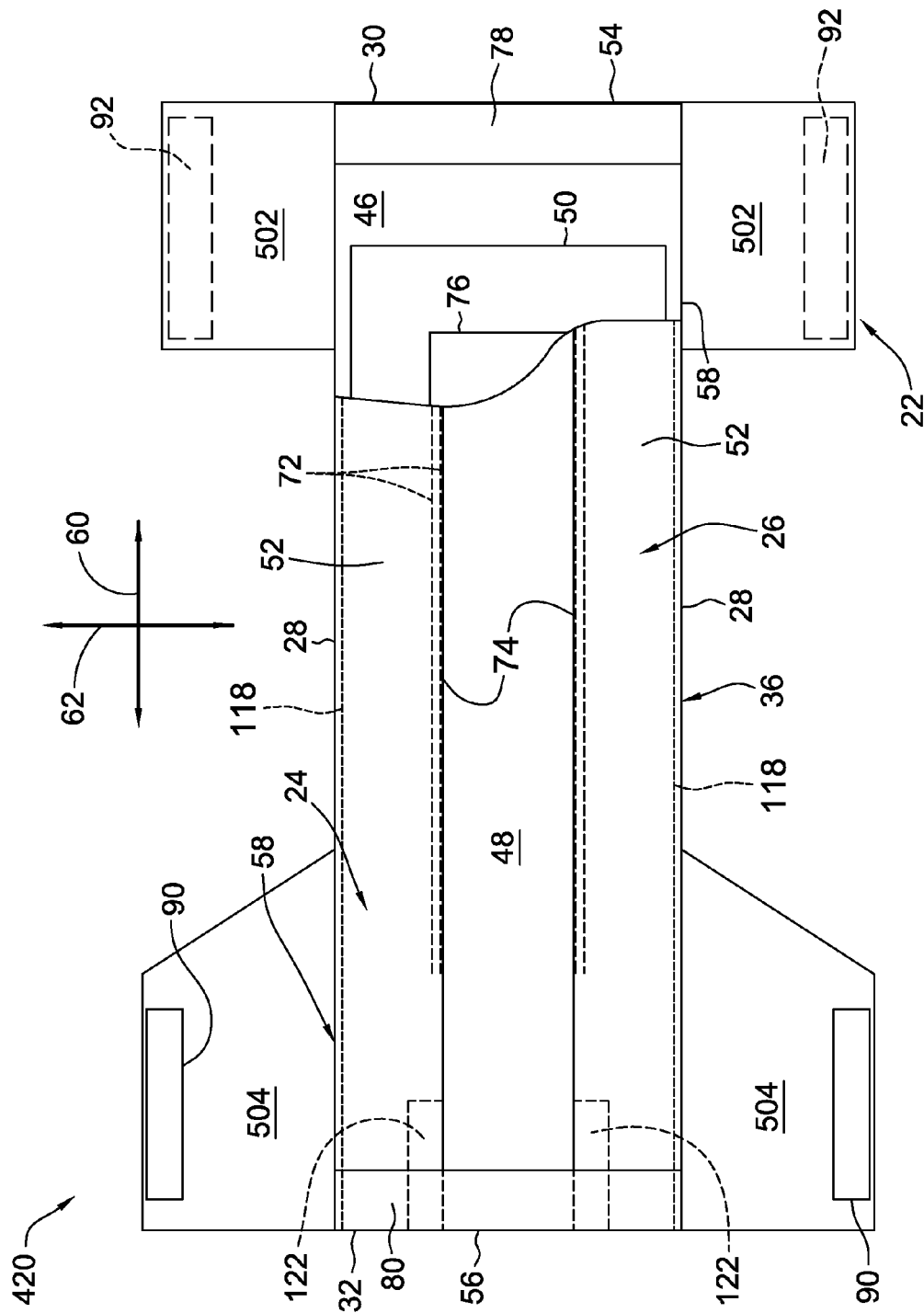
FIG. 9 is a top plan view of another suitable embodiment of an absorbent article in the form of a training pant showing a surface of the training pant adapted to face the wearer when worn, portions of the training pant being cut away to show underlying features.

FIG. 9 illustrates an alternative embodiment of an absorbent article, also in the form of a training pant 420, having discrete front and back side panels 502, 504 formed separately from and secured to the absorbent assembly 36. The side panels 502, 504 are permanently bonded to the absorbent assembly 36 in the respective front and back waist regions 22 and 24 of the pant 420. More particularly, the front side panels 502 can be permanently bonded to and extend transversely outward beyond the side edges 58 of the absorbent assembly 36 at the front waist region 22, and the back side panels 504 can be permanently bonded to and extend transversely outward beyond the side edges 58 of the absorbent assembly 36 at the back waist region 24. The side panels 502 and 504 may be bonded to the absorbent assembly 36 using attachment means known to those skilled in the art such as adhesive, thermal, pressure, or ultrasonic bonding.

The front and back side panels 502, 504, upon wearing of the pants 420, thus comprise the portions of the training pant 420 which are positioned on the hips of the wearer. The front and back side panels 502, 504 can be permanently bonded together to form the three-dimensional configuration of the pant 420, or be releasably connected with one another such as by the fastening components 90, 92 of the illustrated aspects.

In the embodiment of FIG. 9, the side panels 502, 504 comprise an elastic material capable of stretching at least in a direction generally parallel to the lateral axis 62 of the training pant 420. Suitable elastic materials, as well as methods of incorporating elastic side portions into training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference.

Alternatively, the side panel material may include other woven or non-woven materials, such as those described herein as being suitable for construction of the chassis 34 and/or the bodyside liner 48, mechanically pre-strained composites, or stretchable but inelastic materials.

As a result of the containment flaps 52 being integrally formed with the absorbent assembly 36, no additional material is needed along the crotch region 26 of the training pant 20 to attach the containment flaps 52. As a result, the lateral width of the crotch region 26 of the absorbent training pant 20 may be smaller as compared to known training pant, thereby providing a more appealing look and feel. Further, because the containment flaps 52 are integrally formed from the absorbent assembly 36, a continuous liquid impermeable barrier is formed from the bodyside liner 48 and/or the polymer backsheet 46 that extends from the central region of the absorbent assembly out and around the lateral outer sides of the containment flaps 52. As a result, the barrier performance of the containment flaps 52 along the adhesive seams 116 is improved over known absorbent articles, which are generally susceptible to fluid leaks along the attachment seams of containment flaps.

Figure 10:
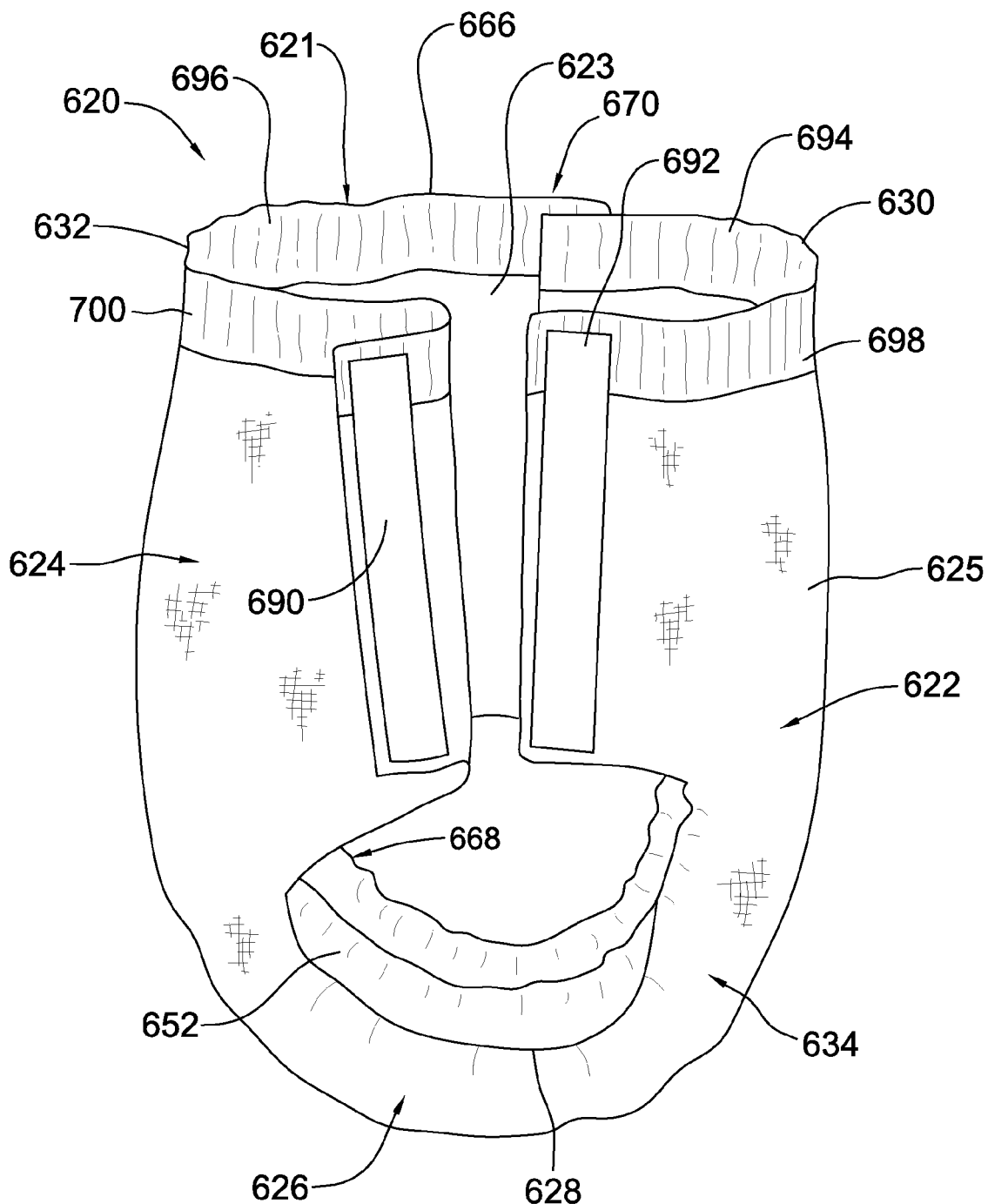
FIG. 10 is a side perspective of another suitable embodiment of an absorbent article shown in the form of a training pant, the training pant having a fully encircling elasticized waistband system including bodyside and garment-side waist elastic members.
Figure 11:
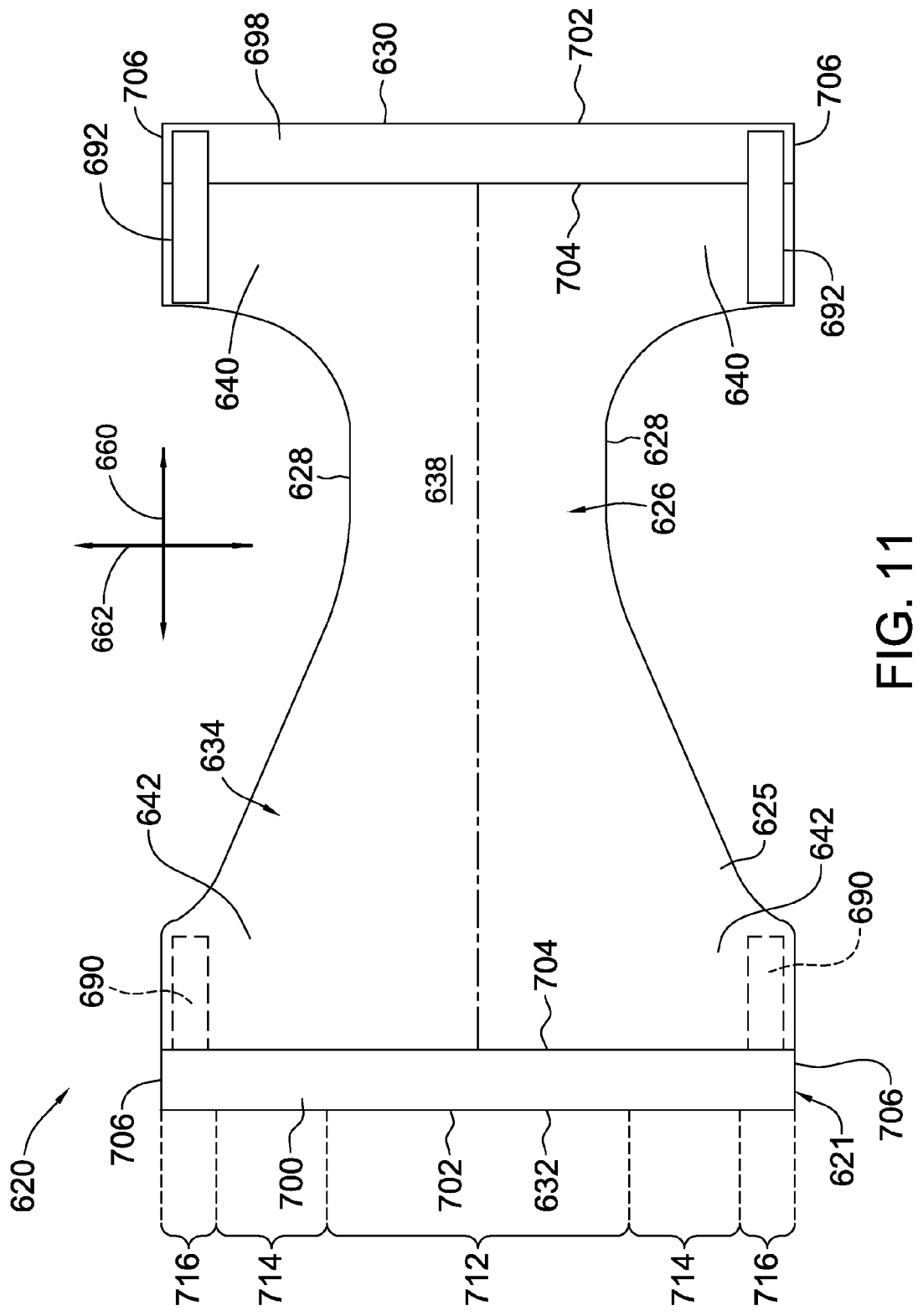
FIG. 11 illustrates a bottom plan view of the absorbent article of FIG. 10 with the training pant in an unfastened, unfolded and laid flat condition, and showing a surface of the training pant adapted to face away from the wearer during use.
Figure 12:
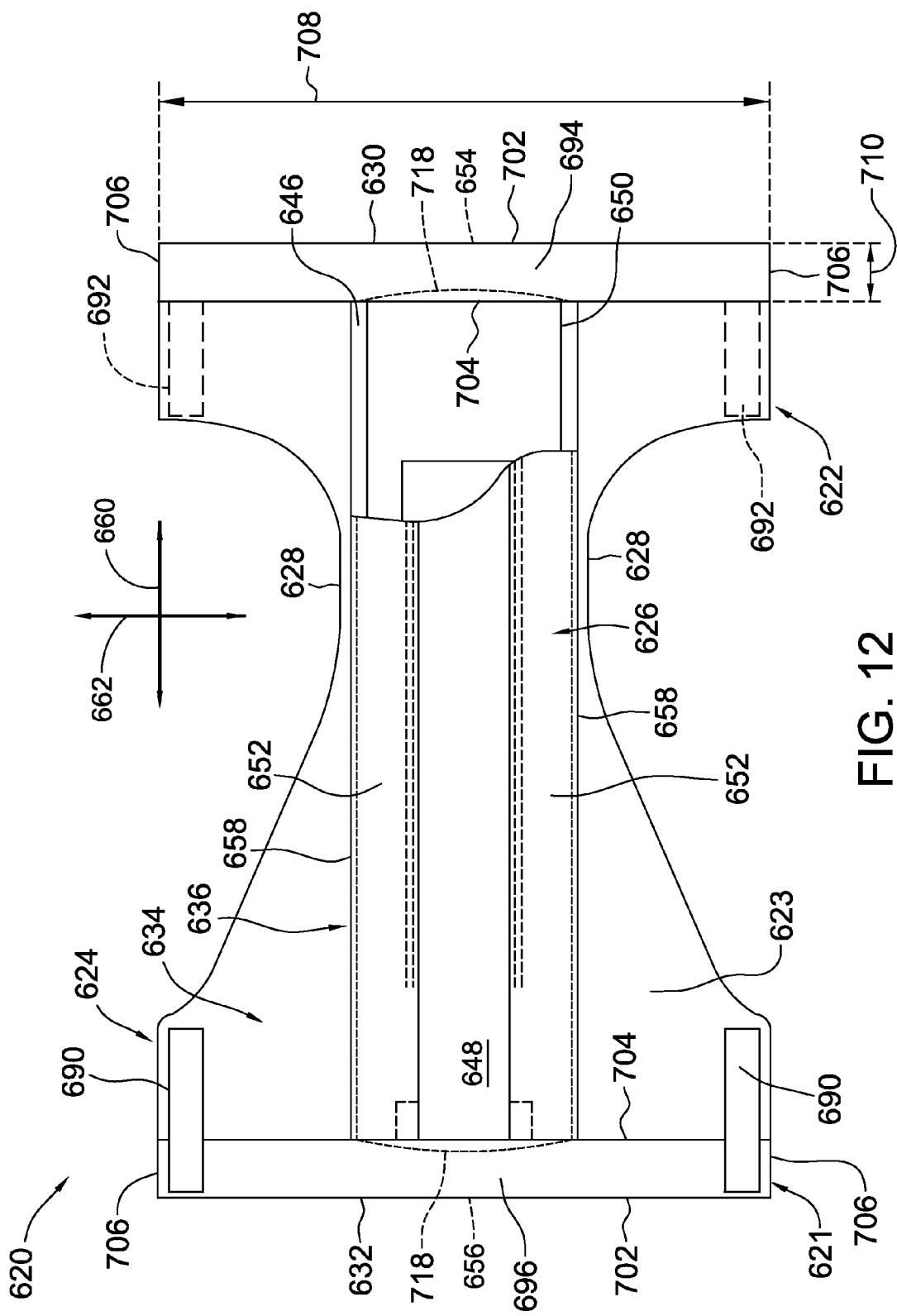
FIG. 12 illustrates a top plan view similar to FIG. 11 but showing a surface of the training pant adapted to face the wearer during use, portions of the training pant being cut away to show underlying features.

Referring now to FIGS. 10-12, yet another suitable embodiment of an absorbent article is shown in the form of a training pant, indicated generally at 620. The training pant 620 illustrated therein is substantially similar to training pant 20 illustrated and described with reference to FIGS. 1-7B, except the training pant 620 of FIGS. 10-12 includes an elasticized waistband system, indicated generally at 621, configured to fully encircle the waist of the wearer during use.

More specifically, the training pant 620 has a front waist region 622, a back waist region 624, and a crotch region 626 disposed longitudinally between and interconnecting the front and back waist regions. The training pant 620 also has a pair of laterally opposite side edges 628 and a pair of longitudinally opposite waist edges, respectively designated as a front waist edge 630 and a back waist edge 632. The training pant 620 also includes a body-facing side 623 (FIG. 12) and a garment-facing side 625 (FIG. 11). Arrows 660 and 662 in FIGS. 11-12 depict the orientation of a longitudinal axis and a transverse or lateral axis, respectively, of the training pant 620.

Similar to the training pant 20 of FIGS. 1-7B, the training pant 620 of FIGS. 10-12 includes a chassis 634 and an absorbent assembly 636 attached to the chassis 634. The chassis 634 includes a longitudinally extending central portion 638, a pair of laterally opposite front side portions 640 extending outward from the central portion 638 at the front waist region 622, and a pair of laterally opposite back side portions 642 extending outward from the central portion at the back waist region 624. In the embodiment illustrated in FIGS. 10-12, the chassis 634 defines the front waist region 622, the back waist region 624, and the crotch region 626 of the training pant 620.

As described above, the front side portions 640, the back side portions 642, and the central portion 638 are formed from the same sheet of material, although it is contemplated that one or more of the front side portions 640, the back side portions 642, and/or the central portion 638 may be formed from two or more separate elements.

The chassis 634 may comprise the same materials and have the same configuration as the chassis 34 described above with reference to FIGS. 1-7B. In the embodiment illustrated in FIGS. 10-12, the chassis 634 (or portions thereof) is suitably elastically extensible. In one suitable embodiment, the chassis 634 is elastically extensible in a lateral direction (i.e., a direction generally parallel to the lateral axis 662 of the training pant 620). In another suitable embodiment, the chassis is elastically extensible in both a lateral direction and a longitudinal direction.

The absorbent assembly 636 illustrated in FIGS. 11-12 may comprise the same materials and have the same configuration as the absorbent assemblies 36, 236 illustrated and described above with reference to FIGS. 1-8B. Specifically, in the illustrated embodiment, the absorbent assembly 636 comprises a liquid impermeable backsheet 646, a bodyside liner 648 attached to the backsheet 646, and an absorbent structure (or absorbent core) 650 disposed between the backsheet 646 and the bodyside liner 648. Similar to the absorbent assembly 36, the absorbent assembly 636 is generally rectangular in shape having a front end 654, a back end 656, and longitudinally extending side edges 658. In the illustrated embodiment, the front and back ends 654, 656 of the absorbent assembly 636 extend to the front and back waist edges 630, 632 of the training pant 620, respectively, and define respective portions of the front and back waist edges 630, 632. It is contemplated, however, that the front end 654 and/or the back end 656 of the absorbent assembly 636 can be spaced inward from the front and back waist edges 630, 632 of the training pant 620.

A pair of containment flaps 652 is integrally formed from the absorbent assembly 636, as described in more detail above with reference to FIGS. 4-7B, for inhibiting the lateral flow of body exudates.

The absorbent assembly 636 of the illustrated embodiment is attached to the chassis 634 along at least the crotch region 626 of the absorbent training pant 620. The absorbent assembly 636 may be attached to the chassis 634 in substantially the same manner as described above with reference to FIGS. 1-7B.

Figure 17:
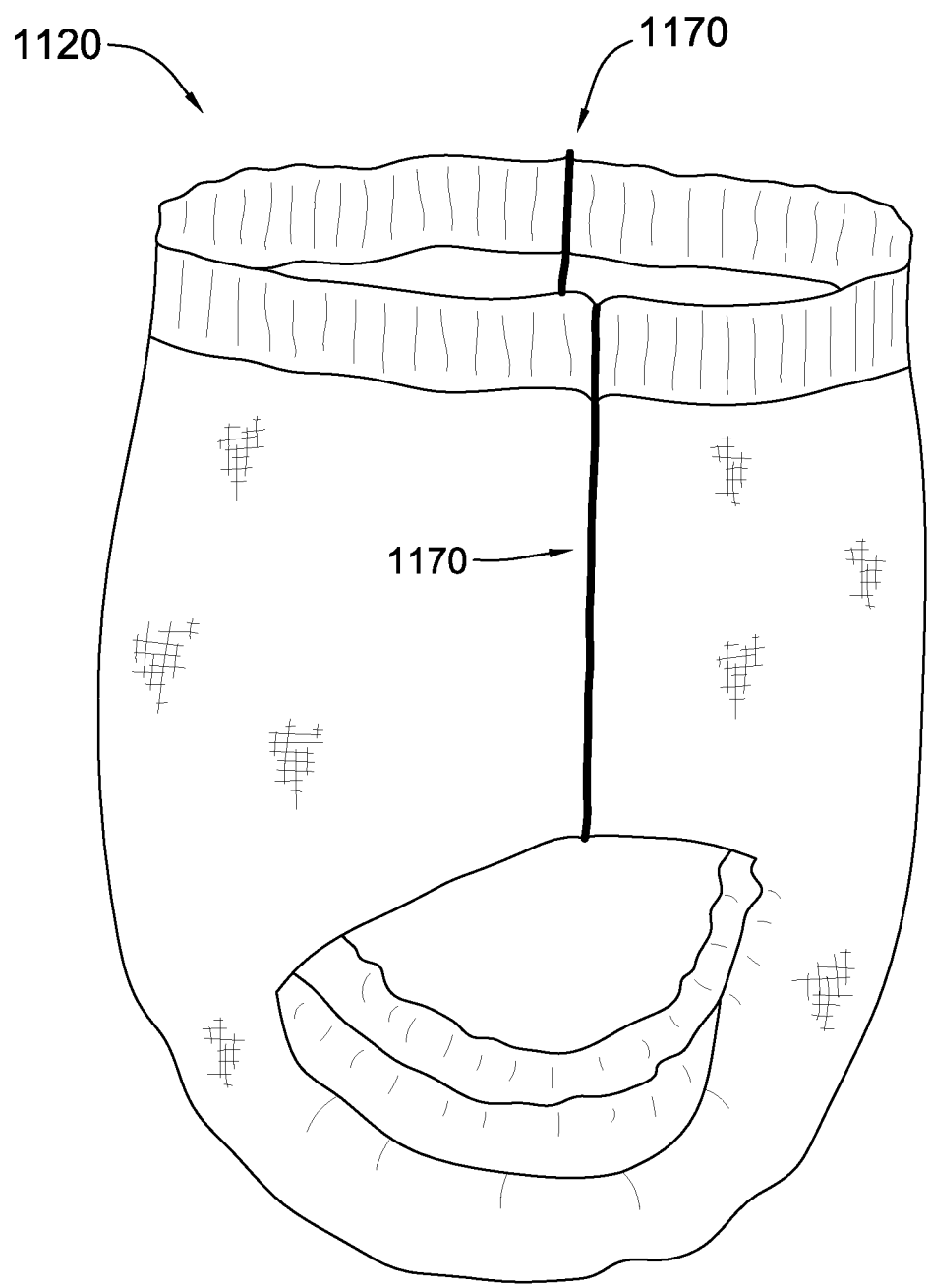
FIG. 17 is a side perspective of another suitable embodiment of an absorbent article shown in the form of a training pant, the training pant having bonded side seams formed along the sides of the training pant.

As with the training pant 20, the training pant 620 has a pair of refastening seams 670 disposed on the side of the pant 620 (one seam being illustrated in FIG. 10). It is understood, however, that the seams can be located at any suitable location on the pant and that the seams can be permanently attached (e.g., by adhesive, thermal bonding, pressure bonding, thermal bonding). For example, the training pant 1120 illustrated in FIG. 17 includes bonded side seams 1170 such as, for example, an overlapping bonded side seam or an abutting side seam. Moreover, while the illustrated refastening seams 670 are defined by a loop fastening components 690 (broadly, a "first fastening component") selectively engagement with hook fastening components 692 (broadly, a "second fastening component"), it is contemplated that any suitable refastenable fasteners can be used such as other types of mechanical fasteners, adhesive fasteners, cohesive fasteners. In one suitable embodiment, for example, the seams are formed by frangible bonds.

With the training pant 620 in a fastened condition, partially illustrated in FIG. 10, the front and back waist regions 622, 624 are attached to each other by the first and second fastening components 690, 692 to define a wear configuration of the pant, having a waist opening 666 and a pair of leg openings 668. The waist edges 630, 632 of the absorbent training pant 620 are configured to encircle the waist of the wearer and together define the waist opening 666 (FIG. 10). Portions of the side edges 628 in the crotch region 626 generally define the leg openings 668.

The absorbent training pant 620, and more specifically the chassis 634, includes an elasticized waistband system 621, described in greater detail below, and leg elastic members (not shown). The leg elastic members can be attached to the inner surface of the chassis 634 and/or the outer surface of the chassis 634 along the opposite side edges 628 and positioned in the crotch region 626 of the absorbent training pant 620. The leg elastic members can be longitudinally aligned along side edges 658 of the absorbent assembly 636, or the leg elastic members can be aligned with the opposite side edges 628 of the absorbent article.

Referring to FIGS. 10-12, the elasticized waistband system 621 of the illustrated embodiment includes a bodyside front waist elastic member 694, a bodyside rear waist elastic member 696, a garment-side front waist elastic member 698, and a garment-side rear waist elastic member 700. The waist elastic members 694, 696, 698, 700 can be formed of any suitable elastic material. Exemplary suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate.

In one suitable embodiment, for example, the waist elastic members 694, 696, 698, 700 comprise a plurality of dry-spun coalesced multifilament spandex elastomeric threads sold under the trade name LYCRA® and available from E. I. Du Pont de Nemours and Company, Wilmington, Del., U.S.A. In another suitable embodiment, the waist elastic members 694, 696, 698, 700 comprise a vertical filament laminate (VFL) material. A VFL is a composite material having at least one gatherable layer such as a non-woven material and at least one elastic layer. One type of vertical filament laminate is disclosed, for example, by U.S. Pat. No. 6,916,750 to Thomas et al., which is incorporated herein by reference. In another suitable embodiment, the waist elastic members 694, 696, 698, 700 comprise an elastic nonwoven composite having an apertured elastic film laminated to one or more nonwoven web materials, examples of which are described in U.S. Pat. No. 7,803,244 issued Sep. 28, 2010 to Siqueira et al., and U.S. Pat. No. 8,361,913 issued Jan. 29, 2013 to Siqueira et al., both of which are incorporated herein by reference. Other suitable elastic materials include single- and dual-faced spandex laminates, stretch-bonded laminates (SBL), and continuous filament stretch-bonded laminates (CFSBL), examples of which are described in U.S. Pat. No. 5,385,775 issued Jan. 31, 1995 to Wright; U.S. Pat. No. 6,057,024 issued May 2, 2000 to Mleziva et al.; and U.S. Pat. No. 6,969,441 issued Nov. 29, 2005 to Welch et al., all of which are incorporated herein by reference.

Figure 15:
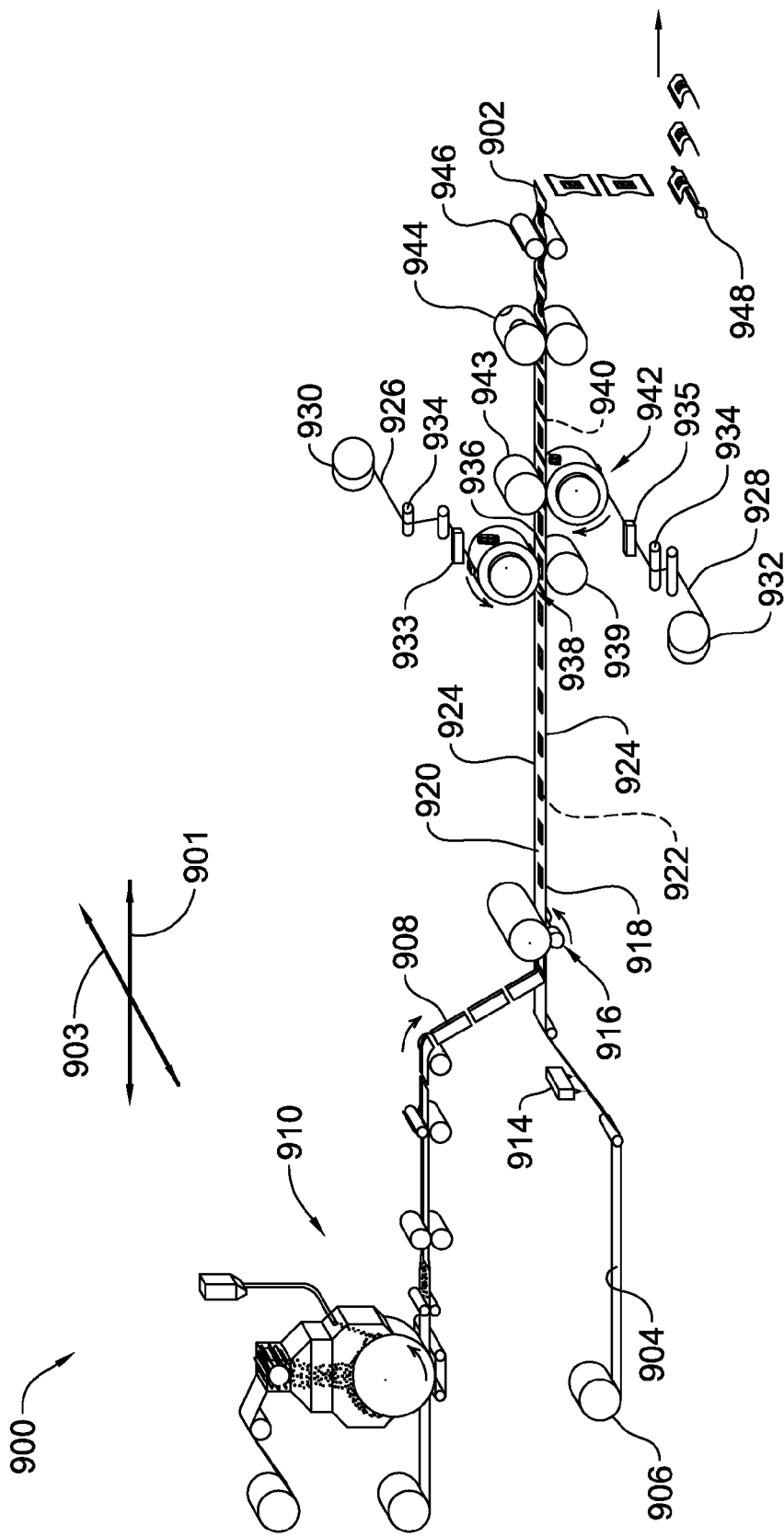
FIG. 15 is a schematic illustrating one suitable method for manufacturing an absorbent article having the fully encircling elasticized waistband system illustrated in FIGS. 10-14.

In one suitable embodiment, the waist elastic members 694, 696, 698, 700 are attached to the training pant 620 in a cross-machine direction using, for example, the process schematically illustrated in FIG. 15. As a result, the waist elastic members 694, 696, 698, 700 are formed separately from one another. In other words, each waist elastic member 694, 696, 698, 700 is a discrete piece of elastic material separate from the other waist elastic members.

Although the elasticized waistband system 621 is illustrated and described as including bodyside front and rear waist elastic members 694, 696 and garment-side front and rear waist elastic members 698, 700, it is understood that in alternative embodiments the elasticized waistband system 621 may include any combination of the bodyside front waist elastic member 694, the bodyside rear waist elastic member 696, the garment-side front waist elastic member 698, and/or the garment-side rear waist elastic member 700.

In the illustrated embodiment, each elastic member 694, 696, 698, 700 is generally rectangular in shape having a top edge 702, a bottom edge 704, and two side edges 706. Each elastic member 694, 696, 698, 700 also has a length 708 (FIG. 12) extending between the side edges 706 and a width 710 (FIG. 12) extending between the top edge 702 and the bottom edge 704. Although the waist elastic members 694, 696, 698, 700 are illustrated and described as being generally rectangular, it is understood that the waist elastic members may have any suitable shape. In one embodiment, for example, the garment-side waist elastic members 698, 700 include undulated and/or scalloped edges.

As seen in FIGS. 11-12, the top edges 702 of the front waist elastic members 694, 698 of the illustrated embodiment are generally aligned with the front waist edge 630 of the training pant 620, and the top edges 702 of the rear waist elastic members 696, 700 of the illustrated embodiment are generally aligned with the back waist edge 632 of the training pant 620. It is understood, however, that the top edges 702 of one or more of the waist elastic members 694, 696, 698, 700 can be spaced from the front waist edge 630 and/or the back waist edge 632. That is, the top edges 702 of the front waist elastic members 694, 698 can be spaced either above or below the front waist edge 630 of the training pant 620, and/or the rear waist elastic members 696, 700 can be spaced either above or below the back waist edge 632 of the training pant 620. In one suitable embodiment, for example, the bodyside front waist elastic member 694 and the garment-side front waist elastic member 698 extend beyond the front waist edge 630, and the bodyside front waist elastic member 694 and the garment-side front waist elastic member 698 are bonded to one another such that the chassis 634 is not visible along the front waist edge 630. Additionally or alternatively, the body-side rear waist elastic member 696 and the garment-side rear waist elastic member 700 extend beyond the back waist edge 632, and the body-side rear waist elastic member 696 and the garment-side rear waist elastic member 700 are bonded to one another such that the chassis 634 is not visible along the back waist edge 632.

In the illustrated embodiment, the top edges 702 of the bodyside waist elastic members 694, 696 are substantially aligned with the top edges 702 of a corresponding garment-side waist elastic member 698, 700. Further, the side edges 706 of the bodyside waist elastic members 694, 696 are substantially aligned with the side edges 706 of a corresponding garment-side waist elastic member 698, 700. As a result, the corresponding bodyside and garment side waist elastic members 694, 696, 698, 700 have a unitary appearance similar to that of waistbands employed in reusable underwear. Further, because the bodyside waist elastic members 694, 696 are at least partially aligned with the garment-side waist elastic members 698, 700, the elasticized waistband system 621 has an increased thickness where the bodyside waist elastic members 694, 696 are aligned with the garment-side waist elastic members 698, 700. Such an increased thickness facilitates gripping and donning the training pant 620, particularly for infants or toddlers whose motor skills are not fully developed. In one suitable embodiment, for example, the thickness of the training pant 620 along the elasticized waistband system is between about 1.0 millimeters and about 6.0 millimeters and, more suitably, between about 2.0 millimeters and about 5.0 millimeters.

As illustrated in FIGS. 11-12, each of the side edges 706 of the front and rear waist elastic members 694, 696, 698, 700 are generally aligned with the side edges 628 of training pant 620. Each of the front and rear waist elastic members 694, 696, 698, 700 extend from one side edge 628 of the training pant 620 to the other, laterally opposing side edge 628 of the training pant 628. The waist elastic members 694, 696, 698, 700 of the illustrated embodiment are configured to fully encircle the waist opening 666 (FIG. 10) and the wearer when training pant 620 is donned in the wearing configuration. It is understood, however, that the side edges 706 of one or more of the waist elastic members 694, 696, 698, 700 can be disposed either outward or inward of the side edges 628 of the training pant. In one suitable embodiment, for example, the side edges 706 of the bodyside rear waist elastic member 696 can terminate adjacent to or in abutting relationship with the first fastening components 690, located on the body-facing side 623 of the back waist region 624, and the garment-side front waist elastic member 698 can terminate adjacent to or in abutting relationship with the second fastening components 692, located on the garment-facing side 626 of the front waist region 622. In another suitable embodiment, one of the bodyside waist elastic members 694, 696 and one of the garment-side waist elastic members 698, 700, collectively fully encircle the waist opening 666 (FIG. 10) and the wearer when training pant 620 is donned in the wearing configuration.

As illustrated in FIGS. 11 and 12, each waist elastic member 694, 696, 698, 700 has substantially the same length 708 and width 710. It is understood, however, that the length 708 and/or width 710 of one or more of the waist elastic members 694, 696, 698, 700 may be different from the length 708 and/or the width 710 of the other waist elastic members 694, 696, 698, 700. In one suitable embodiment, for example, each of the garment-side waist elastic members 698, 700 has a width 710 greater than a width 710 of the bodyside waist elastic members 694, 696.

Each waist elastic member 694, 696, 698, 700 is suitably elastic to facilitate donning the training pant 620, and to facilitate the formation of a seal along the waist edges 630, 632 of the training pant 620. The waist elastic members 694, 696, 698, 700 may have a substantially uniform modulus of elasticity along the length 708 of the respective waist elastic member 694, 696, 698, 700 or, as described below, the modulus of elasticity of one or more waist elastic members 694, 696, 698, 700 may vary along the length 708 of the waist elastic member 694, 696, 698, 700 resulting in a modulus of elasticity profile. As used herein, the term modulus of elasticity refers to a constant that numerically measures or represents the amount of elasticity a material possesses. A high modulus of elasticity, for example, is indicative of a material having a low amount of elasticity. In one suitable embodiment, each waist elastic member 694, 696, 698, 700 has the same modulus of elasticity profile as the other waist elastic members 694, 696, 698, 700. It is understood, however, that one or more waist elastic members 694, 696, 698, 700 may have a modulus of elasticity profile different than the other waist elastic members 694, 696, 698, 700. For example, in one suitable embodiment, the garment-side waist elastic members 698, 700 are less elastic (i.e., have a higher modulus of elasticity) than the bodyside waist elastic members 694, 696 such that the waist elastic members 694, 696, 698, 700 curl inward toward the wearer when placed under tension, thereby providing a body conforming shape.

In the illustrated embodiment, each waist elastic member 694, 696, 698, 700 comprises five regions 712, 714, 716 of varying elasticity (FIG. 11). More specifically, each waist elastic member 694, 696, 698, 700 includes a central region 712, two side-seam regions 714 extending laterally inward from the side edges 706 of the waist elastic members 694, 696, 698, 700, and two lateral outer regions 716 extending between the central region 712 and the adjoining side-seam region 714. Desired moduli of elasticity may be imparted to each region 712, 714, 716 using any suitable method including, for example, selectively cutting or "deadening" the elastic material (e.g., elastic sheets, strands or ribbons) within the waist elastic member 694, 696, 698, 700, or constructing the waist elastic member 694, 696, 698, 700 from discrete pieces of elastic material having desired moduli of elasticity. In one suitable embodiment, the lateral outer regions 716 are more elastic (i.e., have a smaller modulus of elasticity) than the central region 712, and the side-seam regions 714 are less elastic (i.e., have a greater modulus of elasticity) than the central region 712. In one suitable embodiment, the side-seam regions 714 of waist elastic members 694, 696, 698, 700 are non-elastic or "deadened".

Although the illustrated waist elastic members 694, 696, 698, 700 are illustrated and described as having five regions 712, 714, 716 of elasticity, it is understood that the waist elastic members may have more or fewer than five regions of elasticity. In one suitable embodiment, for example, one or more waist elastic members 694, 696, 698, 700 comprise three regions of varying elasticity including a central region 712 and two lateral outer regions 716 extending from the central region 712 to a respective side edge 706 of the waist elastic member 694, 696, 698, 700. It is also contemplated that the waist elastic members can have a single, uniform elasticity along its length.

As noted above, the waist elastic members 694, 696, 698, 700 can be formed of any suitable elastic material including, for example, sheets, strands or ribbons of natural rubber, synthetic rubber, or thermoplastic elastomeric polymers. In one suitable embodiment, each waist elastic member 694, 696, 698, 700 is formed from the same material or materials as the other waist elastic members such that each waist elastic member has substantially the same properties (e.g., elasticity profile, coefficient of friction, softness, etc.) as the other waist elastic members. It is understood, however, that one or more waist elastic members 694, 696, 698, 700 may be formed of different materials to impart desired physical or visual properties to the waist elastic member. In one suitable embodiment, for example, the bodyside waist elastic members 694, 696 have a coefficient of friction greater than a coefficient of friction of the garment-side waist elastic members 698, 700 to facilitate maintaining the position of the training pant 620 on the wearer, and reduce friction between the training pant 620 and garment(s) worn over the training pant 620.

In one suitable embodiment, the presence or noticeability of one or more waist elastic member 694, 696, 698, 700 can be enhanced by providing suitable visual and/or tactile cues (e.g., graphics, color, texturing) on the waist elastic member(s) 694, 696, 698, 700 and/or other components of the training pant 620 (e.g., the chassis 634 and/or the absorbent assembly 636). The visual and/or tactile cues increase the noticeability that the waist elastic members 694, 696, 698, 700 cooperate during use to fully encircle the waist of the wearer. In the illustrated embodiment, for example, each waist elastic member 694, 696, 698, 700 is a different color (e.g., dark blue) than the chassis 634 (e.g., white). Also in the illustrated embodiment, the waist elastic members 694, 696, 698, 700 are applied to the chassis 634 and/or the absorbent assembly 636 under tension, as described below, such that gathers are formed along the waist elastic members 694, 696, 698, 700 when the applied tension is released from the waist elastic members. In another suitable embodiment, the visual cue comprises a scalloped and/or undulated waist elastic member 694, 696, 698, 700.

The bodyside waist elastic members 694, 696 are attached to the body-facing side 623 of the training pant 620 (FIG. 12), and the garment-side waist elastic members 698, 700 are attached to the garment-facing side 626 of the training pant 620 (FIG. 11). In the illustrated embodiment, for example, the waist elastic members 694, 696, 698, 700 are point bonded to the chassis 634.

In embodiments in which the absorbent assembly 636 is interposed between the chassis 634 and the bodyside waist elastic members 694, 696, such as the embodiment illustrated in FIGS. 10-12, the bodyside waist elastic members 694, 696 may also be point bonded to the absorbent assembly 636, such as to the bodyside liner 648 of the absorbent assembly 636. Alternatively, the bodyside waist elastic members 694, 696 may only be bonded to the training pant 620 along the chassis 634. In one suitable embodiment, for example, the bodyside waist elastic members 694, 696 are bonded to a body-facing side of the chassis 634, and are interposed between the absorbent assembly 636 and the chassis 634. In another suitable embodiment, the front and back ends 654, 656 of the absorbent assembly 636 are spaced inward from the bottom edges 704 of the bodyside waist elastic members 694, 696, and the bodyside waist elastic members 694, 696 are bonded to the body-facing side of the chassis 634.

While the waist elastic members 694, 696, 698, 700 may be bonded to the training pant 620 along any suitable portion of the waist elastic member 694, 696, 698, 700, in one suitable configuration, the waist elastic members 694, 696, 698, 700 are bonded with an intermittent bond pattern having a bond area of less than about 25% of the surface area of the waist elastic member 694, 696, 698, 700, more suitably less than about 10% and, even more suitably, less than about 5% of the surface area of the waist elastic member 694, 696, 698, 700. In one suitable embodiment, for example, the waist elastic members 694, 696, 698, 700 are bonded with an intermittent bond pattern having a bond area of about 2% of the surface area of the waist elastic member 694, 696, 698, 700. It is understood, however, that the waist elastic members 694, 696, 698, 700 can be bonded along any suitable portion of the waist elastic member 694, 696, 698, 700.

In alternative embodiments, the elastic waist members 694, 696, 698, 700 can be attached to the chassis 634 and/or the absorbent assembly 636 using an elastic construction adhesive. Suitable elastic construction adhesives include, for example, low tack adhesives having a relatively short open time to inhibit or prevent the adhesive from bonding to unwanted garments or objects.

In some embodiments, such as the illustrated embodiment, the bottom edge 704 of one or both bodyside waist elastic members 694, 696 may be left unattached from the chassis 634 and/or the absorbent assembly 636 such that containment pockets 718 (FIG. 12) are formed along the bottom edge 704 of the bodyside waist elastic member 694, 696 to enhance the containment and absorption of body exudates within the absorbent assembly 636.

Figure 13:
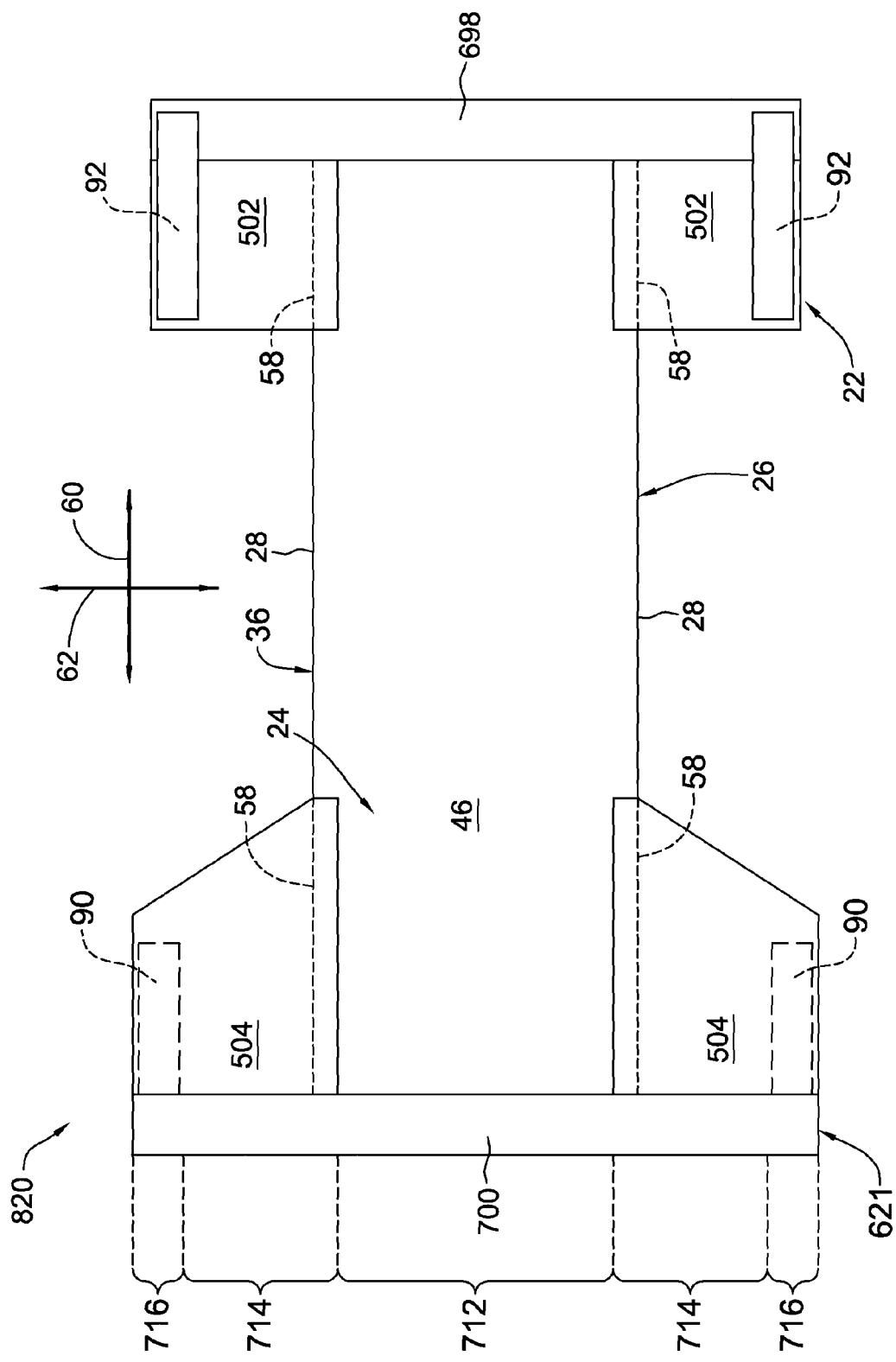
FIG. 13 is a bottom plan view of another suitable embodiment of an absorbent article in the form of a training pant showing a surface of the training pant adapted to face away from the wearer when worn.
Figure 14:
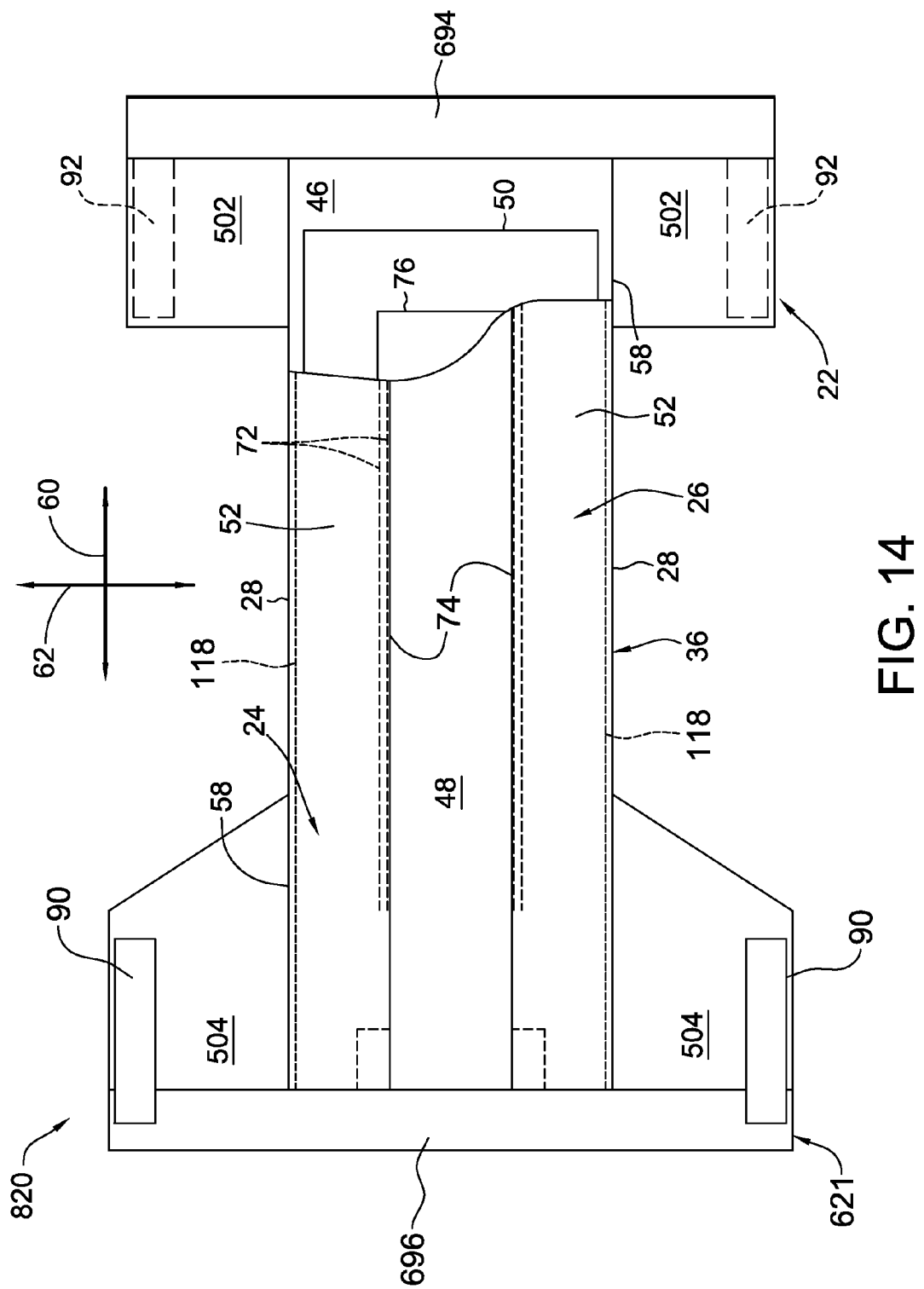
FIG. 14 is a view similar to FIG. 13 but showing a surface of the training pant adapted to face the wearer during use, portions of the training pant being cut away to show underlying features.

FIGS. 13 and 14 illustrate another embodiment of an absorbent article in the form of a training pant, indicated generally at 820. The training pant 820 has discrete front and back side panels 502, 504 formed separately from and secured to the absorbent assembly 36. The training pant 820 is substantially similar to the training pant 420 illustrated and described with reference to FIG. 9, except training pant 820 includes the elasticized waistband system 621 illustrated and described with reference to FIGS. 10-12.

Similar to the training pant 420 illustrated in FIG. 9, the side panels 502, 504 of training pant 820 are permanently bonded to the absorbent assembly 36 in the respective front and back waist regions 22 and 24 of the pant 820. More particularly, the front side panels 502 can be permanently bonded to and extend transversely outward beyond the side edges 58 of the absorbent assembly 36 at the front waist region 22, and the back side panels 504 can be permanently bonded to and extend transversely outward beyond the side edges 58 of the absorbent assembly 36 at the back waist region 24. The side panels 502 and 504 may be bonded to the absorbent assembly 36 using attachment means known to those skilled in the art such as adhesive, thermal, pressure, or ultrasonic bonding.

The front and back side panels 502, 504, upon wearing of the pant 820, thus comprise the portions of the training pant 820 which are positioned on the hips of the wearer. The front and back side panels 502, 504 can be permanently bonded together to form the three-dimensional configuration of the pant 820, or be releasably connected with one another such as by the fastening system 64 of the illustrated aspects.

The side panels 502, 504 may comprise the same materials and have the same configuration as the side panels 502, 504 described above with reference to FIG. 9. In the embodiment of FIGS. 13-14, the side panels 502, 504 comprise an elastic material capable of stretching at least in a direction generally parallel to the lateral axis 62 of the training pant 820.

The waist elastic members 694, 696, 698, 700 of the elasticized waistband system 621 may have any of the configurations described above with reference to FIGS. 10-12.

In the embodiment illustrated in FIGS. 13-14, the front waist elastic members 694, 698 are attached to absorbent assembly 36 and the front side panels 502, and the rear waist elastic members 696, 700 are attached to the absorbent assembly 36 and the back side panels 504. The waist elastic members 694, 696, 698, 700 may be attached using the same methods described above with reference to FIG. 9 (e.g., point bonding, elastic construction adhesive).

With reference to FIG. 13, in one suitable embodiment, the central region 712 of the waist elastic members 694, 696, 698, 700 generally corresponds to the portion of the waist elastic member 694, 696, 698, 700 attached to the absorbent assembly 36. The lateral outer regions 716 and side-seam regions 714 generally correspond to portions of the waist elastic member 694, 696, 698, 700 attached to a respective side panel 502, 504.

The elasticity of the central regions 712, the side-seam regions 714, and the lateral outer regions 716 may be based upon the elasticity or extensibility (or non-extensibility) of the underlying portion of the training pant 820 to which the waist elastic members 694, 696, 698, 700 are attached. In one suitable embodiment, for example, the backsheet 46 and bodyside liner 48 are formed from non-extensible materials, and the front and back side panels 502, 504 are formed from elastically extensible materials. In such an embodiment, the central region 712 of the waist elastic members 694, 696, 698, 700 may suitably be less elastic (i.e., have a higher modulus of elasticity) than the lateral outer regions 716 such that the elastically extensible regions of the waist elastic members 694, 696, 698, 700 generally correspond to the elastically extensible portions of the training pant 820.

FIG. 15 schematically illustrates one suitable assembly 900 for manufacturing an absorbent article 902 having the elasticized waistband system 621 illustrated in FIGS. 10-14. Arrows 901 and 903 in FIG. 15 depict the orientation of a machine direction and a cross-machine direction, respectively, of the assembly 900. As seen in FIG. 15, a continuous supply of material 904 used to form the chassis 34 is provided from a suitable supply source 906 in the machine direction 901. Various components of the absorbent article can be disposed on and/or bonded to the chassis material 904 as the material travels in the machine direction 901, as described below.

A plurality of absorbent assemblies 908 are provided from a suitable supply source such as, for example, an absorbent assembly forming module 910 configured to form the absorbent assembly 36 illustrated and described with reference to FIGS. 1-7B and/or the absorbent assembly 236 illustrated and described with reference to FIGS. 8A and 8B. In the illustrated embodiment, the absorbent assemblies 908 are delivered in the machine direction 901 and disposed intermittently on the continuously moving chassis material 904, one for each absorbent article. In another suitable embodiment, a continuous web assembly including a backsheet, a bodyside liner, and an absorbent structure can be supplied by the absorbent assembly forming module 910 and subsequently cut by a cutter 946 along with the absorbent article 902.

Adhesive can be applied to the chassis material 904 from an adhesive applicator 914 located downstream of the chassis material supply source 906 for adhering the absorbent assemblies 908 to the chassis material 904. The adhesive may be applied continuously or intermittently to the chassis material 904.

In addition to or instead of adhering the absorbent assemblies 908 to the chassis material 904, the absorbent assemblies 908 and chassis material 904 can be transported through a bonding station 916 located downstream of the chassis material supply source 906 and the absorbent assembly supply source 910 to attach the absorbent assemblies 908 to the chassis material 904 and form a continuous web assembly 918 of chassis material 904 and absorbent assemblies 908. In one suitable embodiment, for example, the bonding station 916 includes a laminator roll and/or a chill roll configured to press the absorbent assemblies 908 against the chassis material 904, and adhere the absorbent assemblies 908 to the chassis material 904 with the adhesive applied to the chassis material 904 by the adhesive applicator 914. In another suitable embodiment, the bonding station 916 may include a rotary ultrasonic horn and an anvil roll configured to point bond the absorbent assemblies 908 (e.g., the bodyside liner and/or the backsheet of the absorbent assembly) to the chassis material 904 with or without the adhesive applied by the adhesive applicator 914.

The web assembly 918 has a body-facing side 920 defined by the chassis and the absorbent assembly and a garment-facing side 922 defined by the chassis material 904. The web assembly 918 also includes laterally opposing side edges 924 which, in the illustrated embodiment, are defined by laterally opposing side edges of the chassis material 904.

Two continuous webs of suitable waist elastic materials 926, 928 used to form the bodyside and garment-side waist elastic members 694, 696, 698, 700 (FIGS. 10-14) are provided in the cross-machine direction 903 from suitable supply sources 930, 932, respectively. The supply sources 930, 932 can comprise any suitable mechanism. In the illustrated embodiment, each web of waist elastic material 926, 928 is supplied by a single supply source 930, 932, respectively. It is understood, however, that one or both of the waist elastic materials 926, 928 can be supplied by more than one supply source, such as, for example, two, three, four, five, or any other suitable number of supply sources. Each of the webs of waist elastic material 926, 928 is stretched along the direction in which the webs are fed using a plurality of tensioning rolls 934.

An adhesive applicator 933 applies adhesive to the web of waist elastic material 926 for applying the waist elastic material 926 to the body-facing side 920 of the web assembly 918. Similarly, an adhesive applicator 935 applies adhesive to the web of waist elastic material 928 for applying the waist elastic material 928 to the garment-facing side 922 of the web assembly 918. In one suitable embodiment, the adhesive applicators 933, 935 apply an elastic construction adhesive to the webs of waist elastic material 926, 928, respectively, although any suitable adhesive may be applied by the adhesive applicators 933, 935.

The web of waist elastic material 926 used to form the bodyside waist elastic members 694, 696 is cut to form a plurality of discrete segments 936 of waist elastic material, oriented with respect to the web assembly 918, and applied to the body-facing side 920 of the web assembly 918 at a cutting, orienting, and application station 938. The discrete segments 936 are maintained in a stretched configuration during the cutting, orienting, and application process.

In the illustrated embodiment, the discrete segments 936 are oriented generally in the cross-machine direction 903 before being applied to the web assembly 918, which is traveling in the machine direction 901. Exemplary methods and apparatus for attaching discrete segments in a cross-machine direction to a web moving in a machine direction are described in U.S. Pat. No. 6,899,780 issued May 31, 2005 to Rajala et al., which is incorporated herein by reference. In addition, before the discrete segments 936 are applied to the web assembly 918, the discrete segments 936 may be registered with the position of the web assembly 918 and/or with respect to the position of the web of waist elastic material 928 used to form the garment-side waist elastic members 698, 700 to facilitate proper alignment of the waist elastic members 694, 696, 698, 700 on the absorbent article 902.

The discrete segments 936 of waist elastic material are bonded to the body-facing side 920 of the web assembly 918 at a bonding station 939 using any suitable bonding technique. In one suitable embodiment, the discrete segments 936 of waist elastic material 926 are point bonded to the web assembly 918 using pressure, adhesive, thermal and/or ultrasonic bonding. In another suitable embodiment, the discrete segments 936 of waist elastic material 926 are bonded to the web assembly 918 without the elastic construction adhesive applied by adhesive applicator 933.

The web of waist elastic material 928 used to form the garment-side waist elastic members 698, 700 is attached to the web assembly 918 using a similar process as that used to attach bodyside waist elastic members 694, 696. More specifically, the web of waist elastic material 928 used to form the garment-side waist elastic members 698, 700 is cut into a plurality of discrete segments 940 of waist elastic material, oriented with respect to the web assembly 918, and applied to the garment-facing side 922 of the web assembly 918 at a cutting, orienting, and application station 942. The discrete segments 940 are maintained in a stretched configuration during the cutting, orienting, and application process. In the illustrated embodiment, the discrete segments 940 are oriented generally in the cross-machine direction 903 before being applied to the web assembly 918, which is traveling in the machine direction 901. In addition, before the discrete segments 940 are applied to the web assembly 918, the discrete segments 940 may be registered with the position of the web assembly 918 and/or with respect to the position of the discrete segments 936 used to form the bodyside waist elastic members 694, 696 to facilitate proper alignment of the waist elastic members 694, 696, 698, 700 on the absorbent article 902. In one suitable embodiment, for example, the discrete segments 940 are cut, oriented, stretched, and/or registered with the position of the web assembly 918 such that the laterally opposing side edges of the discrete segments 940 are aligned with the laterally opposing side edges 924 of the web assembly 918 when the discrete segments 940 are attached to the web assembly 918. In another suitable embodiment, both discrete segments 936, 940 are cut, oriented, stretched, and/or registered with the position of the web assembly 918 and with respect to one another such that the laterally opposing side edges of the discrete segments 936, 940 and the web assembly 918 are all aligned when the discrete segments 936, 940 are attached to the web assembly 918.

The discrete segments 940 of waist elastic material are bonded to the garment-facing side 922 of the web assembly 918 at a bonding station 943 using any suitable bonding technique. In one suitable embodiment, the discrete segments 940 of waist elastic material 928 are point bonded to the web assembly 918 using pressure, adhesive, thermal and/or ultrasonic bonding. In another suitable embodiment, the discrete segments 940 of waist elastic material 928 are bonded to the web assembly 918 without the elastic construction adhesive applied by adhesive applicator 935.

As noted above, the discrete segments 936, 940 of waist elastic material are attached to the web assembly 918 under tension such that the discrete segments 936, 940 are attached in an elongated state. The discrete segments 936, 940 of waist elastic material may be applied under any suitable amount of elongation. In one suitable embodiment, for example, the discrete segments 936, 940 are attached to the web assembly 918 at less than 60% elongation of the length of the discrete segment 936, 940, and more suitably, at less than 20% elongation of the length of the discrete segment 936, 940. In the illustrated embodiment, each discrete segment 936, 940 is applied to the web assembly 918 at substantially the same amount of elongation. It is understood, however, that the discrete segments 936, 940 can be applied to the web assembly 918 at differing amounts of elongation. In one suitable embodiment, for example, the discrete segments 936 which form the bodyside waist elastic members 694, 696 are attached to the web assembly 918 under a greater amount of elongation than the discrete segments 940 which form the garment-side waist elastic members 698, 700. The different amounts of elongation between the resulting bodyside elastic members 694, 696 and the garment-side waist elastic members 698, 700 will cause the waist elastic members 694, 696, 698, 700 to curl inward toward the wearer when placed under tension, thereby providing a body conforming shape.

Next in the illustrated embodiment, a shaping mechanism 944 selectively removes portions of the web assembly 918 to provide a desired shape, such as curved side edges for leg openings. Such shaping mechanisms are generally known to those skilled in the art and can include, for example, rotary die cutters, oscillating water cutters, and lasers. Next, a cutter 946 selectively cuts the web assembly 918 into discrete, partially assembled absorbent articles 902. Such cutters 946 are generally known to those skilled in the art and can include, for example, the combination of a cutting roll and an anvil roll through which the web assembly 918 travels. In the illustrated embodiment, the web assembly 918 is cut along a mid-line of at least one of the discrete segments 936, 940 such that a single discrete segment 936, 940 of waist elastic material forms a waist elastic member 694, 696, 698, 700 in two different absorbent articles 902 (e.g., a leading absorbent article and a trailing absorbent article). In the illustrated embodiment, the mid-line is a bisecting line, although it is contemplated that the mid-line along which the discrete segments 936, 940 are cut can be off-set from the center of the discrete segments such that the resulting waist elastic members 694, 696, 698, 700 of a leading absorbent article 902 have a different width than the waist elastic members 694, 696, 698, 700 of a trailing absorbent article 902.

The absorbent articles 902 are then folded at a folding station, indicated generally at 948, using a suitable folding mechanism (e.g., blade folders, linear folders, book folders, tucker blades). In one suitable configuration, the articles 902 are folded about a fold line generally bisecting the training pant. As such, the front and back waist regions 22, 24 of each article are positioned in facing relationship. Once the articles 902 are folded they can be stacked and packaged.

In the embodiment illustrated in FIG. 15, the discrete segments 936, 940 of waist elastic material are illustrated and described as being attached to the web assembly 918 after the absorbent assemblies 908 are attached to the chassis material 904. It is contemplated, however, that the discrete segments 936, 940 of waist elastic material may be attached to the web assembly 918 and/or the chassis material 904 at any suitable time during the process illustrated in FIG. 15. In one suitable embodiment, for example, the discrete segments 936 of waist elastic material are attached to the web of chassis material 904 before the absorbent assemblies 908 are attached to the chassis material 904 such that each discrete segment 936 is interposed between a respective absorbent assembly 908 and the chassis material 904.

Figure 16:
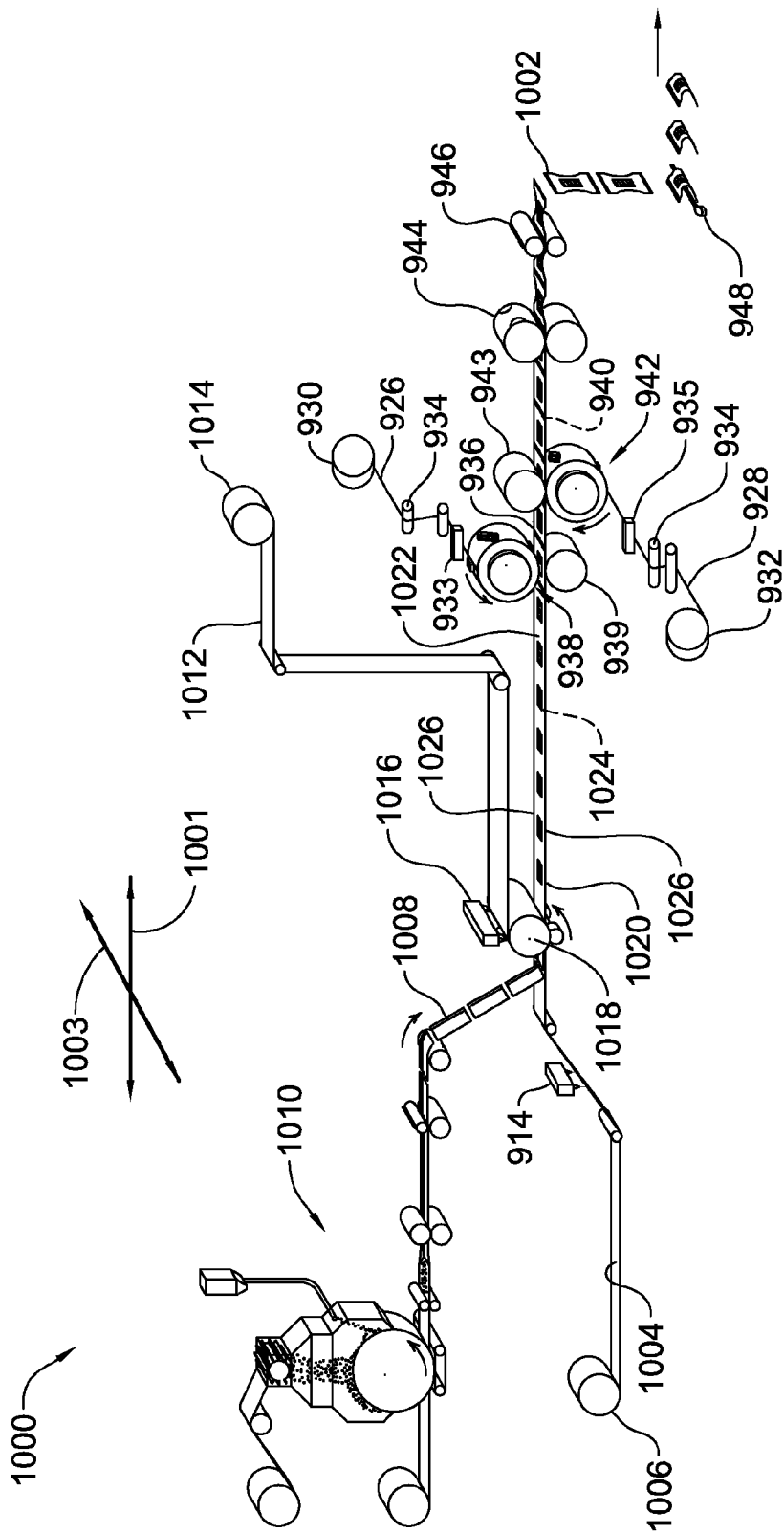
FIG. 16 is a schematic illustrating another suitable method for manufacturing an absorbent article having the fully encircling elasticized waistband system illustrated in FIGS. 10-14.

FIG. 16 schematically illustrates another suitable apparatus 1000 for manufacturing an absorbent article 1002 having the elasticized waistband system 621 illustrated in FIGS. 10-14. The apparatus 1000 is substantially similar to the assembly 900 illustrated in FIG. 15, except the web assembly 1020 of apparatus 1000 is formed from a web of backsheet material 1004, a plurality of absorbent structures 1008, and a web of bodyside liner material 1012.

More specifically, a continuous supply of liquid impermeable backsheet material 1004 is provided from a suitable supply source 1006 in the machine direction 1001.

A plurality of absorbent structures 1008 are provided from a suitable supply source such as, for example, an absorbent structure forming module 1010 configured to form absorbent structures, such as the absorbent structures 50 illustrated and described above with reference to FIGS. 1-7B. In the illustrated embodiment, the absorbent structures 1008 are delivered in the machine direction 1001 and disposed intermittently on the continuously moving backsheet material 1004, one for each absorbent article. The absorbent structures can be bonded to one or more other components using adhesives, or other suitable means.

Similar to the assembly 900, adhesive can be applied to the backsheet material 1004 from an adhesive applicator 914 located downstream of the backsheet material supply source 1006 for adhering the absorbent structures 1008 to the backsheet material 1004.

A continuous web of bodyside liner material 1012 is provided in the machine direction from a suitable supply source 1014. In the illustrated embodiment, an adhesive applicator 1016 applies an adhesive to the web of bodyside liner material 1012, and the web of bodyside liner material 1012 is attached to the web of backsheet material 1004 at a bonding station 1018 to form a web assembly 1020. In one suitable embodiment, for example, the bonding station 1018 includes a laminator roll and/or a chill roll configured to adhere the web of bodyside liner material 1012 to the web of backsheet material 1004. In another suitable embodiment, the bonding station 1018 may include a rotary ultrasonic horn and an anvil roll configured to point bond the bodyside liner material 1012 to the backsheet material 1004.

The web assembly 1020 has a body-facing side 1022 defined by the bodyside liner material 1012 and a garment-facing side 1024 defined by the backsheet material 1004. The web assembly 1020 also includes laterally opposing side edges 1026 which, in the illustrated embodiment, are defined by laterally opposing side edges of the backsheet material 1004.

The waist elastic members 694, 696, 698, 700 are attached to the web assembly 1020 in the same manner as described above with reference to FIG. 15. Specifically, continuous webs of suitable waist elastic materials 926, 928 used to form the bodyside and garment-side waist elastic members 694, 696, 698, 700 (FIGS. 10-14) are provided in the cross-machine direction 1003 from suitable supply sources 930, 932, respectively. The supply sources 930, 932 can comprise any suitable mechanism. In the illustrated embodiment, each web of waist elastic material 926, 928 is supplied by a single supply source 930, 932, respectively. It is understood, however, that one or both of the waist elastic materials 926, 928 can be supplied by more than one supply source, such as, for example, two, three, four, five, or any other suitable number of supply sources. Each of the webs of waist elastic material 926, 928 is stretched along the direction in which the webs are fed using a plurality of tensioning rolls 934.

An adhesive applicator 933 applies adhesive to the web of waist elastic material 926 for applying the waist elastic material 926 to the body-facing side 1022 of the web assembly 1020. Similarly, an adhesive applicator 935 applies adhesive to the web of waist elastic material 928 for applying the waist elastic material 928 to the garment-facing side 1024 of the web assembly 1020. In one suitable embodiment, the adhesive applicators 933, 935 apply an elastic construction adhesive to the webs of waist elastic material 926, 928, respectively, although any suitable adhesive may be applied by the adhesive applicators 933, 935.

The web of waist elastic material 926 used to form the bodyside waist elastic members 694, 696 is cut to form a plurality of discrete segments 936 of waist elastic material, oriented with respect to the web assembly 918, and applied to the body-facing side 920 of the web assembly 918 at a cutting, orienting, and application station 938. The discrete segments 936 are maintained in a stretched configuration during the cutting, orienting and process.

In the illustrated embodiment, the discrete segments 936 are oriented generally in the cross-machine direction 1003 before being bonded to the web assembly 1020, which is traveling in the machine direction 1001. In addition, before the discrete segments 936 are applied to the web assembly 1020, the discrete segments 936 may be registered with the position of the web assembly 1020 and/or with respect to the position of the web of waist elastic material 928 used to form the garment-side waist elastic members 698, 700 to facilitate proper alignment of the waist elastic members 694, 696, 698, 700 on the absorbent article 1002.

The discrete segments 936 of waist elastic material are bonded to the body-facing side 1022 of the web assembly 1020 at the bonding station 939 using any suitable bonding technique. In one suitable embodiment, the discrete segments 936 of waist elastic material 926 are point bonded to the web assembly 1020 using pressure, adhesive, thermal and/or ultrasonic bonding. In another suitable embodiment, the discrete segments 936 of waist elastic material 926 are bonded to the web assembly 1020 without the elastic construction adhesive applied by adhesive applicator 933.

The web of waist elastic material 928 used to form the garment-side waist elastic members 698, 700 is attached to the web assembly 918 using a similar process as that used to attach bodyside waist elastic members 694, 696. More specifically, the web of waist elastic material 928 used to form the garment-side waist elastic members 698, 700 is cut into a plurality of discrete segments 940 of waist elastic material, oriented with respect to the web assembly 1020, and applied to the garment-facing side 1024 of the web assembly 1020 at a cutting, orienting, and application station 942. The discrete segments 940 are maintained in a stretched configuration during the cutting, orienting, and application process. In the illustrated embodiment, the discrete segments 940 are oriented generally in the cross-machine direction 1003 before being applied to the web assembly 1020, which is traveling in the machine direction 1001. In addition, before the discrete segments 940 are applied to the web assembly 1020, the discrete segments 940 may be registered with the position of the web assembly 1020 and/or with respect to the position of the discrete segments 936 used to form the bodyside waist elastic members 694, 696 to facilitate proper alignment of the waist elastic members 694, 696, 698, 700 on the absorbent article 1002. In one suitable embodiment, for example, the discrete segments 940 are cut, oriented, stretched, and/or registered with the position of the web assembly 1020 such that the laterally opposing side edges of the discrete segments 940 are aligned with the laterally opposing side edges 1026 of the web assembly 1020 when the discrete segments 940 are attached to the web assembly 1020. In another suitable embodiment, both discrete segments 936, 940 are cut, oriented, stretched, and/or registered with the position of the web assembly 1020 and with respect to one another such that that the laterally opposing side edges of the discrete segments 936, 940 and the web assembly 1020 are all aligned when the discrete segments 936, 940 are attached to the web assembly 1020.

The discrete segments 940 of waist elastic material are bonded to the garment-facing side 1024 of the web assembly 1020 at the bonding station 943 using any suitable bonding technique. In one suitable embodiment, the discrete segments 940 of waist elastic material 928 are point bonded to the web assembly 1020 using pressure, adhesive, thermal and/or ultrasonic bonding. In another suitable embodiment, the discrete segments 940 of waist elastic material 928 are bonded to the web assembly 1020 using an elastic construction adhesive.

Next in the illustrated embodiment, a shaping mechanism 944 selectively removes portions of the web assembly 1020 to provide a desired shape, such as curved side edges for leg openings. Such shaping mechanisms are generally known to those skilled in the art and can include, for example, rotary die cutters, oscillating water cutters, and lasers. Next, a cutter 946 selectively cuts the web assembly 1020 into discrete, partially assembled absorbent articles 1002. In the illustrated embodiment, the web assembly 1020 is cut along a mid-line of at least one of the discrete segments 936, 940 such that a single discrete segment 936, 940 of waist elastic material forms a waist elastic member 694, 696, 698, 700 in two different absorbent articles 1002 (e.g., a leading absorbent article and a trailing absorbent article). In the illustrated embodiment, the mid-line is a bisecting line, although it is contemplated that the mid-line along which the discrete segments 936, 940 are cut can be off-set from the center of the discrete segments such that the resulting waist elastic members 694, 696, 698, 700 of a leading absorbent article 1002 have a different width than the waist elastic members 694, 696, 698, 700 of a trailing absorbent article 1002.

The absorbent articles 1002 are then folded at a folding station, indicated generally at 948, using a suitable folding mechanism (e.g., blade folders, linear folders, book folders, tucker blades). In one suitable configuration, the articles 1002 are folded about a fold line generally bisecting the training pant. As such, the front and back waist regions 22, 24 of each article are positioned in facing relationship. Once the articles 1002 are folded they can be stacked and packaged.

In the embodiment illustrated in FIG. 16, the discrete segments 936, 940 of waist elastic material are illustrated and described as being attached to the web assembly 1020 after the absorbent structures 1008 are attached to the backsheet material 1004. It is contemplated, however, that the discrete segments 936, 940 of waist elastic material may be attached to the web assembly 1020, the backsheet material 1004, and/or the bodyside liner material 1012 at any suitable time during the process illustrated in FIG. 16. In one suitable embodiment, for example, the discrete segments 936 of waist elastic material are attached to the web of backsheet material 1004 before the absorbent structures 1008 are attached to the backsheet material 1004 such that each discrete segment 936 is interposed between a respective absorbent structure 1008 and the backsheet material 1004.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A method for manufacturing absorbent articles, the method comprising:
    delivering a continuous web assembly including a backsheet material, a liquid permeable bodyside liner material, and an absorbent structure interposed between the backsheet material and the bodyside liner material, the web assembly having a body-facing side and a garment-facing side;
    attaching a discrete segment of first waist elastic material to the body-facing side of the web assembly;
    attaching a discrete segment of second waist elastic material to the garment-facing side of the web assembly such that the web assembly is interposed between the discrete segments of first and second waist elastic materials;
    attaching a discrete segment of third waist elastic material to the body-facing side of the web assembly;
    attaching a discrete segment of fourth waist elastic material to the garment-facing side of the web assembly such that the web assembly is interposed between the discrete segments of third and fourth waist elastic materials; and
    cutting the web assembly to form a plurality of absorbent articles.

2. The method as set forth in claim 1 wherein at least one of attaching the discrete segment of first waist elastic material and attaching the discrete segment of second waist elastic material comprises:
    moving a web of waist elastic material;
    cutting the web of waist elastic material into a plurality of discrete segments of waist elastic material;
    orienting the discrete segments of waist elastic material in a cross-machine direction; and
    attaching the discrete segments of waist elastic material to the web assembly in the cross-machine direction.

3. The method as set forth in claim 1 further comprising:
    registering one of the discrete segments of first waist elastic material and second waist elastic material with the web assembly; and
    registering the other of the discrete segments of first waist elastic material and second waist elastic material with the discrete segment of waist elastic material registered with the web assembly.

4. The method as set forth in claim 1 wherein the web assembly includes laterally opposing side edges, the discrete segment of second waist elastic material includes laterally opposing side edges, and attaching the discrete segment of second waist elastic material includes attaching the discrete segment of second waist elastic to the garment-facing side of the web assembly such that the side edges of the discrete segment are substantially aligned with the side edges of the web assembly.

5. The method as set forth in claim 1 wherein cutting the web assembly comprises cutting the discrete segment of first waist elastic material and the discrete segment of second waist elastic material along a mid-line to form two absorbent articles each having at least one bodyside waist elastic member and at least one garment-side waist elastic member.

6. The method as set forth in claim 1 wherein at least one of the discrete segment of first waist elastic material and the discrete segment of second waist elastic material are stretched in the cross-machine direction before being attached to the web assembly.

7. The method as set forth in claim 1 wherein the discrete segment of first waist elastic material is attached to the web assembly under a greater amount of elongation than the discrete segment of second waist elastic material.

8. The method as set forth in claim 1 wherein attaching at least one of the discrete segment of first waist elastic material and the discrete segment of second waist elastic material comprises at least one of thermal bonding, pressure bonding, adhesive bonding, and ultrasonic bonding.

9. The method as set forth in claim 1 wherein at least one of attaching the discrete segment of first waist elastic material and attaching the discrete segment of second waist elastic material comprises attaching the discrete segment of waist elastic material using an elastic construction adhesive.

10. The method as set forth in claim 1 wherein the backsheet material comprises a liquid impermeable material.

11. A method for manufacturing absorbent articles, the method comprising:
    delivering a continuous web assembly including a backsheet material, a liquid permeable bodyside liner material, and an absorbent structure interposed between the backsheet material and the bodyside liner material, the web assembly having a body-facing side and a garment-facing side;
    attaching a discrete segment of first waist elastic material to the body-facing side of the web assembly to define a bodyside front waist elastic member;
    attaching a discrete segment of second waist elastic material to the garment-facing side of the web assembly to define a garment-side front waist elastic member such that the web assembly is interposed between the discrete segments of first and second waist elastic materials;
    attaching a discrete segment of third waist elastic material to the body-facing side of the web assembly to define a bodyside rear waist elastic member;
    attaching a discrete segment of fourth waist elastic material to the garment-facing side of the web assembly to define a garment-side rear waist elastic member such that the web assembly is interposed between the discrete segments of third and fourth waist elastic materials; and
    cutting the web assembly to form a plurality of absorbent articles.

12. The method as set forth in claim 11 further comprising stretching the discrete segment of first waist elastic material before attaching the discrete segment of first waist elastic material to the body-facing side of the web assembly.

13. The method as set forth in claim 12 further comprising stretching the discrete segment of second waist elastic material before attaching the discrete segment of second waist elastic material to the garment-facing side of the web assembly.

14. The method as set forth in claim 13 wherein the discrete segment of first waist elastic material is stretched a greater amount than the discrete segment of second waist elastic material.

15. The method as set forth in claim 11 further comprising:
    supplying a first continuous web of waist elastic material to a cutting station;
    cutting the first continuous web of waist elastic material at the cutting station to define a plurality of the discrete segments of first waist elastic material;
    supplying a second continuous web of waist elastic material to a cutting station; and
    cutting the second continuous web of waist elastic material at the cutting station to define a plurality of the discrete segments of second waist elastic material.

16. The method as set forth in claim 11 further comprising registering the discrete segment of second waist elastic material in opposed relationship with the first waist elastic material before attaching the discrete segment of second waist elastic material to the garment-facing side of the web assembly.

17. The method as set forth in claim 16 wherein attaching the discrete segment of second waist elastic material to the garment-facing side of the web assembly comprises point bonding the discrete segment of second waist elastic material to the garment-facing side of the web assembly.

18. A method for manufacturing absorbent articles, the method comprising:
    delivering a continuous web assembly including a backsheet material, a liquid permeable bodyside liner material, and an absorbent structure interposed between the backsheet material and the bodyside liner material, the web assembly having a body-facing side and a garment-facing side;
    attaching a discrete segment of first waist elastic material to the body-facing side of the web assembly to define a bodyside rear waist elastic member;
    attaching a discrete segment of second waist elastic material to the garment-facing side of the web assembly to define a garment-side rear waist elastic member such that the web assembly is interposed between the discrete segments of first and second waist elastic materials;
    attaching a discrete segment of third waist elastic material to the body-facing side of the web assembly to define a bodyside front waist elastic member;
    attaching a discrete segment of fourth waist elastic material to the garment-facing side of the web assembly to define a garment-side front waist elastic member such that the web assembly is interposed between the discrete segments of third and fourth waist elastic materials; and
    cutting the web assembly to form a plurality of absorbent articles.

19. The method as set forth in claim 18 further comprising stretching the discrete segment of first waist elastic material before attaching the discrete segment of first waist elastic material to the body-facing side of the web assembly.

20. The method as set forth in claim 19 further comprising stretching the discrete segment of second waist elastic material before attaching the discrete segment of second waist elastic material to the garment-facing side of the web assembly.

21. The method as set forth in claim 20 wherein the discrete segment of first waist elastic material is stretched a greater amount than the discrete segment of second waist elastic material.

22. The method as set forth in claim 18 further comprising:
   supplying a first continuous web of waist elastic material to a cutting station;
   cutting the first continuous web of waist elastic material at the cutting station to define a plurality of the discrete segments of first waist elastic material;
   supplying a second continuous web of waist elastic material to a cutting station; and
   cutting the second continuous web of waist elastic material at the cutting station to define a plurality of the discrete segments of second waist elastic material.

23. The method as set forth in claim 18 further comprising registering the discrete segment of second waist elastic material in opposed relationship with the first waist elastic material before attaching the discrete segment of second waist elastic material to the garment-facing side of the web assembly.

24. The method as set forth in claim 23 wherein attaching the discrete segment of second waist elastic material to the garment-facing side of the web assembly comprises point bonding the discrete segment of second waist elastic material to the garment-facing side of the web assembly.

* * * * *